United States Patent
Bardy et al.

(10) Patent No.: US 10,849,523 B2
(45) Date of Patent: *Dec. 1, 2020

(54) SYSTEM AND METHOD FOR ECG DATA CLASSIFICATION FOR USE IN FACILITATING DIAGNOSIS OF CARDIAC RHYTHM DISORDERS

(71) Applicant: Bardy Diagnostics, Inc., Seattle, WA (US)

(72) Inventors: Gust H. Bardy, Carnation, WA (US); Ezra M. Dreisbach, Vashon, WA (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,312

(22) Filed: Apr. 8, 2019

(65) Prior Publication Data

US 2019/0231210 A1 Aug. 1, 2019

Related U.S. Application Data

(60) Continuation of application No. 15/934,888, filed on Mar. 23, 2018, now Pat. No. 10,251,576, which is a (Continued)

(51) Int. Cl.
*A61B 5/0432* (2006.01)
*A61B 5/0456* (2006.01)
(Continued)

(52) U.S. Cl.
CPC .......... *A61B 5/0456* (2013.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

DE 19955211 5/2001
EP 1859833 11/2007
(Continued)

OTHER PUBLICATIONS https://en.wikipedia.org/wiki/Convolutional_neural_network#Receptive_fields_in_the_visual_cortex (Year: 2017).*
(Continued)

*Primary Examiner* — Kennedy Schaetzle
(74) *Attorney, Agent, or Firm* — Krista A. Wittman

(57) ABSTRACT

A system and method for ECG data classification for use in facilitating diagnosis of cardiac rhythm disorders is provided. ECG data is obtained via an electrocardiography monitor shaped for placement on a patient's chest. The ECG data is divided into segments and noise detection analysis is applied to the ECG data segments. A noise classification or a valid classification is assigned to each segment of the ECG data. At least one ECG data segment assigned the noise classification and that includes ECG data that corresponds with feedback from the patient via the electrocardiography monitor is identified. The ECG data that corresponds with the patient feedback is removed from the identified ECG data segment with the noise classification. The ECG data segments assigned the noise classification are removed from further analysis.

18 Claims, 17 Drawing Sheets

Related U.S. Application Data continuation-in-part of application No. 15/231,752, filed on Aug. 8, 2016, now Pat. No. 10,045,709, which is a continuation of application No. 15/066,883, filed on Mar. 10, 2016, now Pat. No. 9,408,551, which is a continuation-in-part of application No. 14/997,416, filed on Jan. 15, 2016, now Pat. No. 9,345,414, which is a continuation-in-part of application No. 14/614,265, filed on Feb. 4, 2015, now Pat. No. 9,408,545, which is a continuation-in-part of application No. 14/488,230, filed on Sep. 16, 2014, now Pat. No. 9,700,227, which is a continuation-in-part of application No. 14/080,725, filed on Nov. 14, 2013, now Pat. No. 9,730,593, said application No. 15/934,888 is a continuation-in-part of application No. 15/785,317, filed on Oct. 16, 2017, now Pat. No. 9,936,875, which is a continuation of application No. 15/362,743, filed on Nov. 28, 2016, now Pat. No. 9,788,722, which is a division of application No. 14/875,622, filed on Oct. 5, 2015, now Pat. No. 9,504,423.

(60) Provisional application No. 62/132,497, filed on Mar. 12, 2015, provisional application No. 61/882,403, filed on Sep. 25, 2013, provisional application No. 62/591,715, filed on Nov. 28, 2017.

(51) Int. Cl.

| | | |
|---|---|---|
| *A61B 5/044* | (2006.01) | |
| *A61B 5/04* | (2006.01) | |
| *A61B 5/00* | (2006.01) | |
| *A61B 5/0408* | (2006.01) | |
| *A61B 5/0452* | (2006.01) | |
| *A61B 5/046* | (2006.01) | |
| *A61B 5/0464* | (2006.01) | |
| *A61B 5/0245* | (2006.01) | |
| *A61B 5/024* | (2006.01) | |
| *A61B 5/0205* | (2006.01) | |
| *A61B 5/0468* | (2006.01) | |

(52) U.S. Cl.
CPC .......... *A61B 5/02405* (2013.01); *A61B 5/044* (2013.01); *A61B 5/046* (2013.01); *A61B 5/04011* (2013.01); *A61B 5/04017* (2013.01); *A61B 5/0432* (2013.01); *A61B 5/0464* (2013.01); *A61B 5/04085* (2013.01); *A61B 5/04087* (2013.01); *A61B 5/04525* (2013.01); *A61B 5/6823* (2013.01); *A61B 5/7203* (2013.01); *A61B 5/0468* (2013.01); *A61B 5/742* (2013.01)

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |

(56) References Cited

U.S. PATENT DOCUMENTS

| | | |
|---|---|---|
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 10,251,576 B2 * | 4/2019 | Bardy .................. A61B 5/044 |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 * | 3/2004 | Cao ..................... A61B 5/0456 600/521 |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |

(56) References Cited

U.S. PATENT DOCUMENTS

| | | |
|---|---|---|
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0054737 A1 | 3/2006 | Richardson |
| 2006/0084883 A1 | 4/2006 | Linker |
| 2006/0100530 A1* | 5/2006 | Kliot ............... A61B 5/0002 600/483 |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0177168 A1 | 12/2008 | Callahan et al. |
| 2008/0306359 A1 | 12/2008 | Zdeblick et al. |
| 2008/0312522 A1 | 12/2008 | Rowlandson et al. |
| 2009/0012412 A1 | 1/2009 | Wiesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |

(56) References Cited

U.S. PATENT DOCUMENTS

| | | |
|---|---|---|
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2017/0112399 A1 | 4/2017 | Brisben et al. |
| 2017/0156592 A1* | 6/2017 | Fu ..................... A61B 5/7221 |
| 2017/0281032 A1 | 10/2017 | Weinberg et al. |
| 2017/0366921 A1 | 12/2017 | Pflugh et al. |
| 2018/0078771 A1 | 3/2018 | Koop et al. |
| 2019/0021671 A1 | 1/2019 | Kumar et al. |
| 2019/0059763 A1 | 2/2019 | Shakur et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |
| WO | 2017072250 | 5/2017 |

OTHER PUBLICATIONS

Pranav Rajpurkar et al. "Cardiologist-Level Arrhythmia Detection with Convolutional Neural Networks," arxiv.org, Cornell University Library, 201 Olin Library Cornell University Ithaca, NY 14853, Jul. 6, 2017 (Jul. 6, 2017), XP080774895.

Pourbabaee Bahareh et al. "Feature Learning with Deep Convolutional Neural Networks for Screening Patients with Paroxysmal Atrial Fibrillation," 2016 Neural Networks (IJCNN), 2016 International Joint Conference on Neural getworks (IJCNN), IEEE, Jul. 24, 2016 (Jul. 24, 2016), pp. 5057-5064, XP032992832, DOI: 10.1109/IJCNN.2016.7727866.

Xiong Zhaohan et al. "Robust ECG Signal Classification for Detection of Atrial Fibrillation Using a Novel Neural Network," 2017 Computing in Cardiology (CinC), CCAL, Sep. 24, 2017 (Sep. 24, 2017), pp. 1-4, XP033343575, DOI: 10.22489/CinC.2017.066-138.

15 of the Hottest Wearable Gadgets, URL <http://thehottestgadgets.com/2008/09/the-15-hottest-wearable-gadgets-001253> (Web page cached on Sep. 27, 2008).

Alivecor, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; eI-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

(56) References Cited

OTHER PUBLICATIONS

Kligfield, Paul et al., Recommendations for the Standardization and Interpretation of the Electrocardiogram: Part I. J.Am.Coll. Cardiol; 2007; 49; 1109-27, 75 Pgs.
Lauren Gravitz, "When Your Diet Needs a Band-Aid," Technology Review, MIT. (May 1, 2009).
Lieberman, Jonathan, "How Telemedicine Is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.
McManus et al., "A Novel Application for the Detection of an Irregular Pulse using an iPhone 4S in Patients with Atrial Fibrillation," vol. 10(3), pp. 315-319 (Mar. 2013.).
Nike+ Fuel Band, URL <http://www.nike.com/us/en_us/c/nikeplus-fuelband> (Web page cached on Jan. 11, 2013.).
P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).
Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2013.).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.).
Zio Patch System, URL <http://www.irhythmtech.com/zio-solution/zio-system/index.html> (Web page cached on Sep. 8, 2013.).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.

Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/j.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
https://web.archive.org/web/20130831204020/http://www.biopac.com/research.asp?CatID=37&Main=Software (Aug. 2013).
Adinstruments:ECG Analysis Module for LabChart & PowerLab, 2008.
BIOPAC Systems, Inc. #AS148—Automated ECG Analysis , Mar. 24, 2006.
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
http://www.gtec.at/Products/Software/g.BSanalyze-Specs-Features (2014).

* cited by examiner

270

290

300

320

SYSTEM AND METHOD FOR ECG DATA CLASSIFICATION FOR USE IN FACILITATING DIAGNOSIS OF CARDIAC RHYTHM DISORDERS

CROSS-REFERENCE TO RELATED APPLICATION

This non-provisional patent application is a continuation of U.S. Pat. No. 10,251,576, issued Apr. 9, 2019, which is a continuation-in-part of U.S. Pat. No. 10,045,709, issued Aug. 14, 2018, which is a continuation of U.S. Pat. No. 9,408,551, issued Aug. 9, 2016, which is a continuation-in-part of U.S. Pat. No. 9,345,414, issued May 24, 2016, which is a continuation-in-part of U.S. Pat. No. 9,408,545, issued Aug. 9, 2016, which is a continuation-in-part of U.S. Pat. No. 9,700,227, issued Jul. 11, 2017, which is a continuation-in-part of U.S. Pat. No. 9,730,593, issued Aug. 15, 2017; and of which is also a continuation-in-part of U.S. Pat. No. 9,936,875, issued Apr. 10, 2018, which is a continuation of U.S. Pat. No. 9,788,722, issued Oct. 17, 2017, which is a division of U.S. Pat. No. 9,504,423, issued Nov. 29, 2016; and this non-provisional patent application further claims priority under 35 U.S.C. § 119(e) to U.S. Provisional Patent application, Ser. No. 62/132,497, filed Mar. 12, 2015, U.S. Provisional application, Ser. No. 61/882,403, filed Sep. 25, 2013, and U.S. Provisional application, Ser. No. 62/591,715, filed Nov. 28, 2017, the disclosures of which are incorporated by reference.

FIELD

This application relates in general to electrocardiographic monitoring and, in particular, to a system and method for ECG data classification for use in facilitating diagnosis of cardiac rhythm disorders with the aid of a digital computer.

BACKGROUND

An ECG procedure measures cardiac electrical potentials that can be graphed to visually depict the electrical activity of the heart over time and allows physicians to diagnose cardiac function by visually tracing the cutaneous electrical signals (action potentials) that are generated by the propagation of the transmembrane ionic currents that trigger the depolarization of cardiac fibers. Conventionally, a standardized set format 12-lead configuration is used by an ECG machine to record cardiac electrical signals from well-established traditional chest locations.

An ECG trace contains alphabetically-labeled waveform deflections, PQRSTU, that represent distinct features within the cyclic cardiac activation sequence and that can be interpreted post-ECG recordation to derive heart rate and physiology and for use in medical diagnosis and treatment. The P-wave represents atrial depolarization, which causes atrial contraction. The QRS-complex represents ventricular depolarization and is the largest electrical signal of the heart. The T-wave and U-wave represents ventricular repolarization. The T and U-waves are not usually used in diagnosing most cardiac rhythm disorders and are included for completeness.

Here, the focus is around the R-wave, which is often used as an abbreviation for the QRS-complex. When measuring the time between an R-R interval, one can get a beat-by-beat assessment of heart rate. Typically, the R-R interval span between successive R-waves, in a normal heart, is 600 milliseconds (ms) to 1000 ms (i.e., one second) long, which respectively corresponds to 100 to 60 beats per minute (bpm). If one further considers the R-R interval as occurring over time, beat-by-beat, detailed cardiac physiology data may be embedded to provide information that allows a physician to understand, at a glance, the context of the associated ECG rhythm both before and after a suspected rhythm abnormality and can be of confirmational and collaborative value in cardiac arrhythmia diagnosis and treatment.

Conventionally, the potential of R-R interval context has not been fully realized, partly due to the difficulty of presentation in a concise and effective manner to physicians. For instance, routine ECGs are typically displayed at an effective paper speed of 25 millimeters (mm) per second. A lower speed is not recommended because ECG graph resolution degrades at lower speeds and diagnostically-relevant features may be lost. Conversely, a half-hour ECG recording, progressing at 25 mm/s, results in 45 meters of ECG waveforms that, in printed form, is cumbersome and, in electronic display form, will require significant back and forth toggling between pages of waveforms, as well as presenting voluminous data transfer and data storage concerns. As a result, ECGs are less than ideal tools for diagnosing cardiac arrhythmia patterns that only become apparent over an extended time frame, such as 10 minutes or longer.

In addition to or in lieu of physician review, the R-wave data can be provided to analysis software for identification of cardiac events and patient diagnosis. However, such software generally operates best on datasets that represent a few minutes to two days of ECG data. As newer ECG monitoring devices enter the market, many include longer data recording periods. Accordingly, such analysis programs are overloaded with data, which can hinder effectiveness of the analysis, leading to an incorrect patient diagnosis.

Further, performing an analysis of data that includes large amounts of noise can affect accuracy of patient diagnosis. For instance, noise can mask portions of the ECG data, which can prevent analysis software or a medical professional from identifying patterns of cardiac events, as well as lead to an incorrect diagnosis or lack of a diagnosis.

Therefore, a need remains for improving quality of ECG data, while reducing amounts of the ECG data for analysis, including patient diagnosis, by identifying and removing noise. Such noise can be recognized by differentiating regions of valid ECG data from noise using an adaptive noise detector and the regions of noise can be removed from the valid ECG data.

SUMMARY

ECG data is recorded for a patient via an ECG ambulatory monitor over an extended period of time. The recorded ECG data is provided to an adaptive noise detector prior to differentiating valid ECG data from noise. The noise can appear as device-related events and lead to an inaccurate diagnosis. The ECG data identified as noise can be removed and the remaining valid ECG data is then provided to a medical professional or analysis software for analysis and patient diagnosis.

Patent feedback received during recording can be helpful to identify cardiac events. For instance, patients are instructed to press a tactile feedback button on the ECG ambulatory monitor when they feel discomfort, ill, or that a cardiac event may be occurring. However, pressure on the button can often appear as noise and may be removed. To prevent removal of the data associated with the button press, a window surrounding the button press is designated. Any ECG data classified as noise and overlapping the window is removed from the noise classification and remains with the ECG data for analysis via software or a medical professional.

One embodiment provides a system and method for ECG data classification for use in facilitating diagnosis of cardiac rhythm disorders. ECG data is obtained via an electrocardiography monitor shaped for placement on a patient's chest. The ECG data is divided into segments and noise detection analysis is applied to the ECG data segments. A noise classification or a valid classification is assigned to each segment of the ECG data. At least one ECG data segment assigned the noise classification and that includes ECG data that corresponds with feedback from the patient via the electrocardiography monitor is identified. The ECG data that corresponds with the patient feedback is removed from the identified ECG data segment with the noise classification. The ECG data segments assigned the noise classification are removed from further analysis.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

DETAILED DESCRIPTION

A normal healthy cardiac cycle repeats through an expected sequence of events that can be visually traced through an ECG. Each cycle starts with cardiac depolarization originating high in the right atrium in the sinoatrial (SA) node before spreading leftward towards the left atrium and inferiorly towards the atrioventricular (AV) node. After a delay in the AV node, the depolarization impulse transits the Bundle of His and moves into the right and left bundle branches and Purkinje fibers to activate the right and left ventricles.

Figure 1:
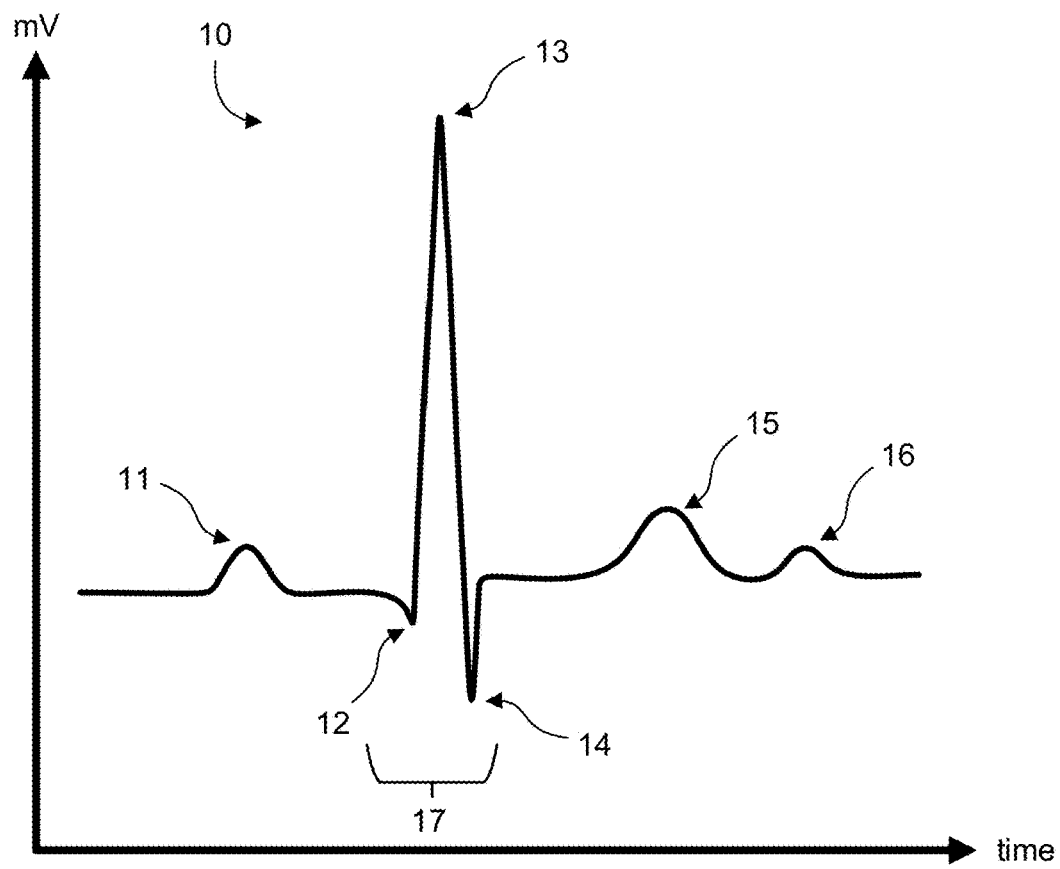
FIG. 1 is a graph showing, by way of example, a single ECG waveform.

When a rhythm disorder is suspected, diagnostically-relevant arrhythmic events in the cardiac cycle can often be identified and evaluated with the assistance of an ECG and R-R interval tachography, somewhat similar to Poincaré plots. Routine ECG evaluation is primarily focused on identifying changes to expected ECG waveform shapes. R-R interval tachographs are focused on showing heart rate trends prior to and after an arrhythmia. This information is critical to understanding the underpinnings of arrhythmia onset and offset, both features critical to managing the patient regardless of the specific arrhythmia shown on the ECG. FIG. 1 is a graph showing, by way of example, a single ECG waveform 10. The x-axis represents approximate time in units of tenths of a second and the y-axis represents approximate cutaneous electrical signal strength in units of millivolts. By long-standing convention, ECGs are typically printed or displayed at an effective paper speed of 25 millimeters (mm) per second. Although in practice an ECG may be provided to a physician in traditional paper-printed form, in "virtual" electronic display form, or both. Nevertheless, the term "effective paper speed" is still widely applied as a metric to normalize the recorded ECG signal to a standardized grid of 1 mm squares (omitted for the sake of clarity in FIG. 1), whereby each 1 mm horizontal box in the grid corresponds to 0.04 s (40 ms) of recorded time. Other effective paper speeds, grid sizes and units of display are possible.

A full ECG consists of a stream of alphabetically-labeled waveforms 10 that collectively cover cardiac performance over a period of observation. For a healthy patient, within each ECG waveform 10, the P-wave 11 will normally have a smooth, normally upward, positive waveform that indicates atrial depolarization. The QRS complex 17 will usually follow during normal rhythms, often with a downward deflection of a Q-wave 12, followed by a larger upward deflection of an R-wave 13, and be terminated with a downward waveform of the S-wave 14, which are collectively representative of ventricular depolarization. This term, QRS, is often reduced to the "R-wave". Thus, reference to the R-R interval means the time from one R-wave (or QRS) to another R-wave. For completeness sake of showing the full ECG, we identify the T-wave 15, which will normally be a modest upward waveform, representative of ventricular repolarization, while the U-wave 16, which is often not directly observable, will indicate the recovery period of the Purkinje conduction fibers. For the purposes of the R-R plot, this part of the ECG waveform will not be pertinent.

Rhythm disorders often manifest through R-R interval variability or through the patterns formed by R-R intervals over an extended time period prior to and after a specific arrhythmia onset and offset. Both are important tools in the diagnosis of cardiac rhythm amonibnormalities. For example, atrial fibrillation (AF) is the chaotic firing of the atria that leads to an erratic activation of the ventricles. AF is initially diagnosed by an absence of organized P-waves 11 and confirmed by erratic ventricular rates that manifest in an ECG R-R interval plot as a cloud-like pattern of irregular R-R intervals due to an abnormal conduction of impulses to the ventricles. There is a Gaussian-like distribution to these R-R intervals during AF. Similarly, atrial flutter (AFL) is an abnormal heart rhythm in which cardiac impulses travel along pathways within the right atrium in an organized circular motion, causing the atria to beat faster than and out of sync with the ventricles. During AFL, the heart beats quickly, yet with a regular pattern. Although AFL presents in an ECG in a "sawtooth" pattern, AFL behavior can fluctuate wildly. Such fluctuation can be confirmed in an ECG by characteristic R-R interval patterns that usually manifest as 2:1 atrioventricular (AV) conduction, 4:1 AV conduction or even variable AV conduction, as it frequently can be. The importance of this latter manifestation of AFL relates to how AFL can be distinguished from AF. The R-R interval plot can clearly distinguish the two unlike algorithms that frequently conflate AF with AFL and variable conduction.

Figure 2:
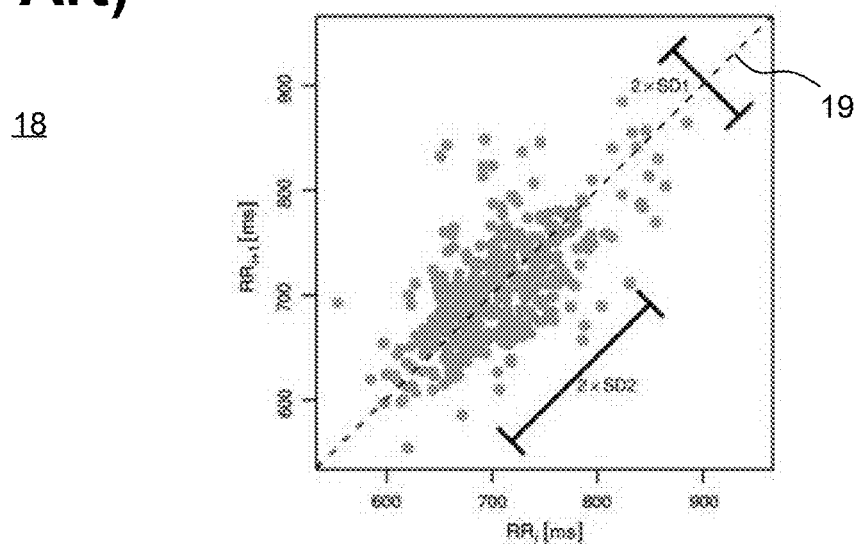
FIG. 2 is a graph showing, by way of example, a prior art Poincaré R-R interval plot.

Conventionally, R-R intervals have been visualized using Poincare plots. FIG. 2 is a graph showing, by way of example, a prior art Poincare R-R interval plot 18. The x-axis represents the duration of R-R interval n in units of milliseconds (ms). The y-axis represents the duration of R-R interval n+1 also in units of ms. Ordinarily, the x- and y-axes use the same units, so as to form a trend line 19 along the 45-degree angle. When an R-R interval is equal to the successive R-R interval, as often occurs when heart rhythm is regular, the dot representing the two intervals falls onto the 45-degree trend line 19. Conversely, when an R-R interval has changed since the preceding R-R interval, the dot representing the two intervals falls off the 45-degree trend line 19 and, as the difference between successive R-R intervals increases, the dots fall further away from the trend line 19.

The number of dots deviating from the trend line 19 in a Poincare plot can indicate the frequency of occurrence of irregular heartbeats when compared to the number of dots on the trend line 19. The distance of the dots to the trend line 19 can approximate the extent of heart rate change from one heartbeat to the next. However, as heart rate change is limited to only successively-occurring heartbeats, the linearity of time and associated contextual information over an extended time frame are lost. Poincare plots can be generally predictive but they have limited value when used to understand physiological antecedents to an arrhythmia pre- and post-rhythm events, for example something as simple as exercise. In addition, significant changes in heart rate, particularly spikes in heart rate, such as due to sinus rhythm transitions to atrial flutter, may be masked, distorted or even omitted in a Poincare plot if the change occurs over non-successive heartbeats. In summary, a Poincare plot is more useful as a mathematical tool than a physiological one, and therefore a Poincare plot cannot truly represent what the heart is doing serially over time with respect to changes in the heart's normal and abnormal physiology on a beat-by-beat basis.

Figure 3:
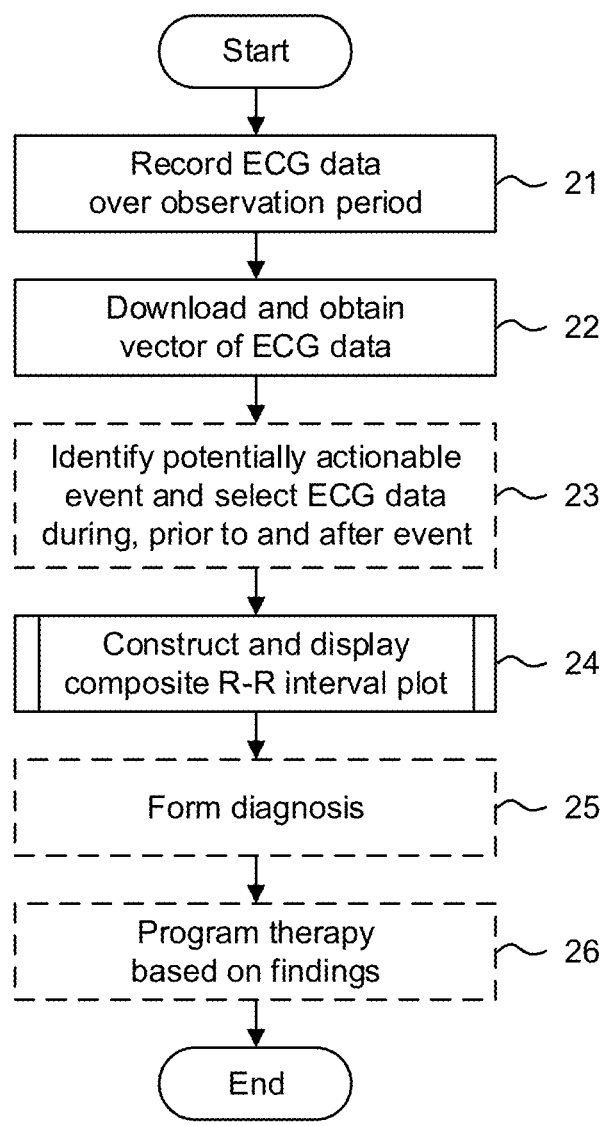
FIG. 3 is a flow diagram showing a method for facilitating diagnosis of cardiac rhythm disorders with the aid of a digital computer in accordance with one embodiment.

Despite the limitations of Poincaré plots and related forms of R-R interval tachography, R-R interval data when presented in a format duplicating temporal physiological events manifest on an actual ECG remains a key tool that physicians can rely upon to identify temporally-related cardiac dysrhythmic patterns. Interpretation of R-R interval data can be assisted by including multiple temporal points of reference and a plot of R-R interval data that comparatively depicts heart rate variability in concert with R-R interval data. FIG. 3 is a flow diagram showing a method 20 for facilitating diagnosis of cardiac rhythm disorders with the aid of a digital computer in accordance with one embodiment. The method 20 can be implemented in software and execution of the software can be performed on a computer, such as further described infra with reference to FIG. 14, as a series of processes or method modules or steps.

As a precursor step, the patient's ECG data are recorded over a set time period (step 21), which can be over a short term or extended time frame. ECG recordation, as well as other physiological monitoring, can be provided through various kinds of ECG-capable monitoring ensembles, including a standardized 12-lead ECG setup, such as used for clinical ECG monitoring, a portable Holter-type ECG recorder for traditional ambulatory ECG monitoring, or a wearable ambulatory ECG monitor, such as a flexible extended wear electrode patch and a removable reusable (or single use) monitor recorder, such as described in commonly-assigned U.S. Pat. No. 9,345,414, issued May 24, 2016, the disclosure of which is incorporated by reference. The wearable ambulatory ECG monitor includes an electrode patch and monitor recorder that are synergistically optimized to capture electrical signals from the propagation of low amplitude, relatively low frequency content cardiac action potentials, particularly the P-waves, generated during atrial activation, and is described in further detail below with respect to FIG. 15. Still other forms of ECG monitoring assemblies are possible.

Figure 14:
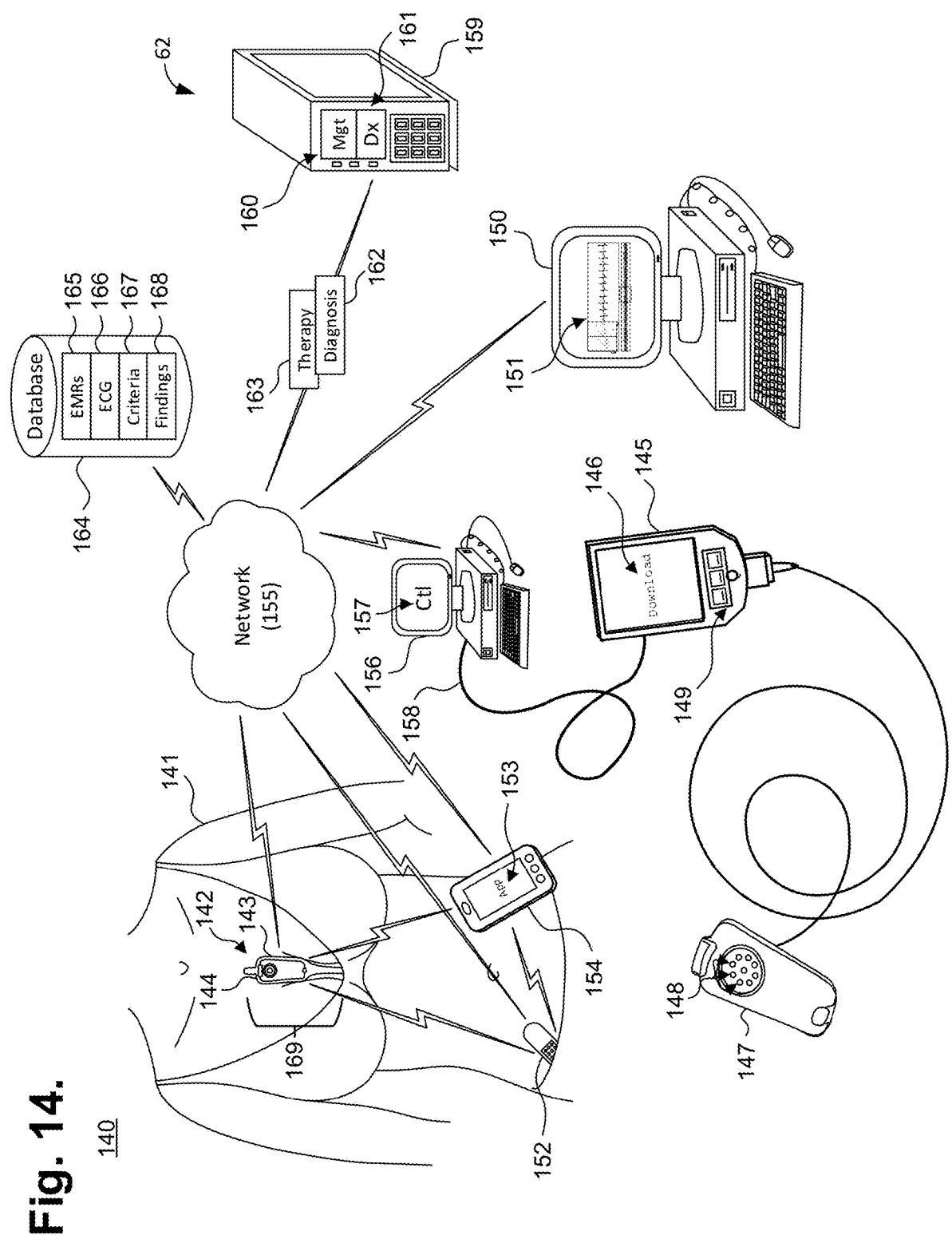
FIG. 14 is a block diagram showing a system for facilitating diagnosis of cardiac rhythm disorders with the aid of a digital computer in accordance with one embodiment.

Upon completion of the monitoring period, the ECG and any other physiological data are downloaded or retrieved into a digital computer, as further described infra with reference to FIG. 14, with, for instance, the assistance of a download station or similar device, or via wireless connection, if so equipped, and a vector of the downloaded or retrieved ECG data is obtained (step 22). In one embodiment, the vector of ECG data represents a 40-minute (or other duration) time span that is used in constructing the plot of R-R interval data, although other pre-event and post-event time spans are possible. Optionally, a potentially-actionable cardiac event within the vector of ECG data can be identified and the ECG data during, prior to and after the event is selected (step 23). The event could be identified with the assistance of a software package, such as Holter LX Analysis Software, licensed by NorthEast Monitoring, Inc., Maynard, Mass.; Intelli Space Cardiovascular Image and Information management system, licensed Koninklijke Philips N.V., Amsterdam, Netherlands; MoMe System, licensed by InfoBionic, Lowell, Mass.; Pyramis ECG Management, licensed by Mortara Instrument Inc., Milwaukee, Wis.; ICS Clinical Suite, licensed by Spacelabs Healthcare Inc., Snoqualmie, Wash.; or a customized software package. Alternatively, the potentially-actionable cardiac event could be identified by a physician or technician during review of the ECG data.

Figure 4:
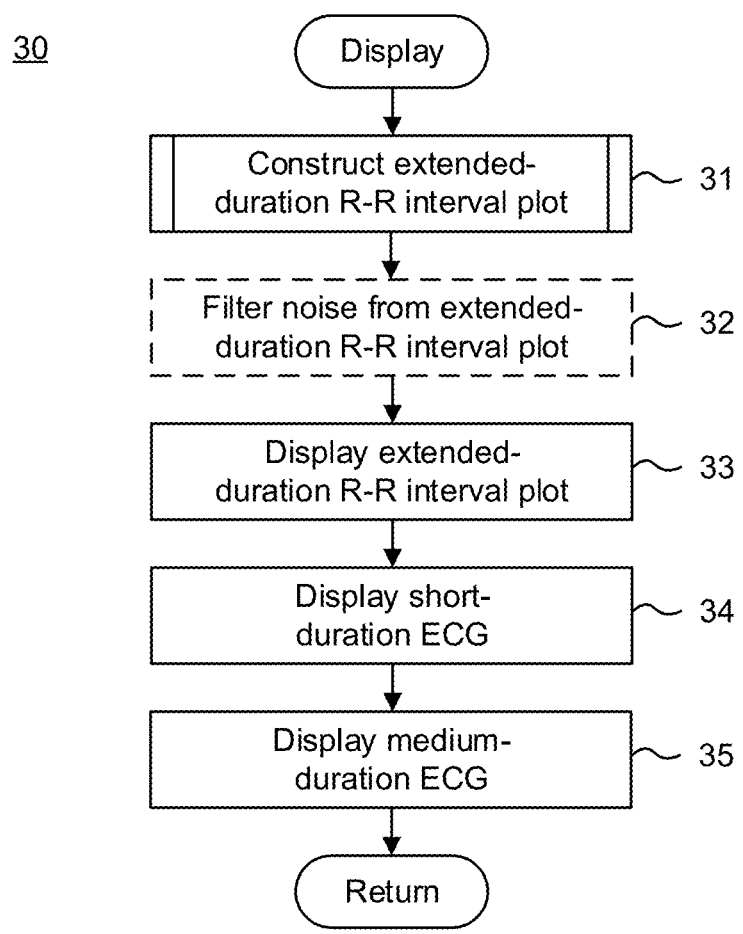
FIG. 4 is a flow diagram showing a routine for constructing and displaying a diagnostic composite plot for use in the method of FIG. 3.

To improve diagnosis of heart rate variability, a diagnostic composite plot is constructed that includes one or more temporal points of reference into the ECG data, which provide important diagnostic context, and a plot of R-R interval data is constructed based on the vector of ECG data (step 24), as further described infra with reference to FIG. 4. Briefly, both near field and far field contextual views of the ECG data are constructed and displayed. Both views are temporally keyed to an extended duration R-R interval data view that, in one embodiment, is scaled non-linearly (for practical viewing reasons) to maximize the visual differentiation for frequently-occurring heart rate ranges, such that a single glance allows the physician to make a diagnosis. The use of a non-linear heart rate scale adjacent to the ECG prevents a skewing of the R-R data to exceed the visual format of a page of paper. Thus, all three views are presented simultaneously, in a visually convenient format that can present 3 sequential ECG data sets per page, thereby allowing the interpreting physician to diagnose rhythm and the pre- and post-contextual events leading up to a cardiac rhythm of interest in a reading and storage friendly manner.

In a further embodiment, findings made through interpretation of heart rate variability patterns in the diagnostic composite plot can be analyzed to form a diagnosis of a cardiac rhythm disorder (step 25), such as the cardiac rhythm disorders listed, by way of example, in Table 1. For instance, the heart rate variability patterns in the diagnostic composite plot could be provided to a system that programmatically detects AF by virtue of looking for the classic Gaussian-type distribution on the "cloud" of heart rate variability formed in the plot of R-R interval data, which can be corroborated by the accompanying contextual ECG data. Finally, therapy to address diagnosed disorder findings can optionally be programmed into a cardiac rhythm therapy delivery device (step 26), such as an implantable medical device (IMD) (not shown), including a pacemaker, implantable cardioverter defibrillator (ICD), or similar devices.

TABLE 1

Cardiac Rhythm Disorders

Normal sinus rhythm
Sinus Bradycardia
Sinus Tachycardia

TABLE 1-continued

Cardiac Rhythm Disorders

Premature atrial and ventricular beats
Ectopic atrial tachycardia
Atrial fibrillation
Atrial flutter
Atrial or ventricular bigeminy, trigeminy or quadrigeminy
Sinus Bradycardia
Fusion beats
Interpolated ventricular premature beats
Intraventricular conduction delay
Junctional rhythm
AV Nodal re-entrant tachycardia
AV re-entrant tachycardia
Wolff-Parkinson-White Syndrome and Pre-excitation
Ventricular tachycardia
Accelerated idioventricular rhythm
AV Wenckebach block
AV Type II block
Sinoatrial block A diagnostic composite plot is constructed and displayed to help physicians identify and diagnose temporally-related cardiac dysrhythmic patterns. The diagnostic composite plot includes ECG traces from two or more temporal points of reference and a plot of R-R interval data, although other configurations of ECG data plots when combined with the R-R interval plot will also provide critical information. FIG. 4 is a flow diagram showing a routine 30 for constructing and displaying a diagnostic composite plot for use in the method 20 of FIG. 3. Specific examples of diagnostic composite plots are discussed in detail infra with reference to FIGS. 7-13.

In the diagnostic composite plot, R-R interval data is presented to physicians in a format that includes views of relevant near field and far field ECG data, which together provide contextual information that improves diagnostic accuracy. In a further embodiment, other views of ECG data can be provided in addition to or in lieu of the near field and far field ECG data views. The near field (or short duration) ECG data provides a "pinpoint" classical view of an ECG at traditional recording speed in a manner that is known to and widely embraced by physicians. This near field ECG data is coupled to a far field (or medium duration) ECG data view that provides an "intermediate" lower resolution, offering pre- and post-event contextual ECG data. Thus, the extended-duration R-R interval plot is first constructed (step 31), as further described infra with reference to FIG. 5. Optionally, noise can be filtered from the R-R interval plot (step 32), which is then displayed (step 33). In a further embodiment, noise can be filtered from the ECG data prior to constructing the R-R interval plot, as further described below with reference to FIG. 19. Noise filtering can include low-pass or high-pass filtering or other forms of signal processing, including automatic gain control, such as described in commonly-assigned U.S. Pat. No. 9,345,414, issued May 24, 2016, cited supra, as well as identification via an adaptive noise detector, as further described in detail below with respect to FIGS. 19-25.

Rhythm disorders have different weightings depending upon the context with which they occur. In the diagnostic composite plot, the R-R interval data view and the multiple views of the ECG data around which the R-R data embrace, provide that necessary context. Effectively, the short and medium duration ECG data that accompanies the extended-duration R-R interval plot represents the ECG data "zoomed" in around a temporal point of reference identified in the center (or other location) of the R-R interval plot, thereby providing a short-term, medium-term and long-term visual context to the physician that allows temporal assessment of cardiac rhythm changes in various complementary views of the heart's behavior. The durations of the classical "pinpoint" view, the pre- and post-event "intermediate" view, and the R-R interval plot are flexible and adjustable. In one embodiment, the diagnostic composite plot displays R-R interval data over a forty-minute duration and ECG data over short and medium durations (steps 34 and 35), such as four-second and 24-second durations that provide two- and 12-second segments of the ECG data before and after the RR interval plot's temporal point of reference, which is generally in the center of the R-R interval plot, although other locations in the R-R interval plot could be identified as the temporal point of reference. The pinpoint "snapshot" and intermediate views of ECG data with the extended term R-R interval data comparatively depicts heart rate context and patterns of behavior prior to and after a clinically meaningful arrhythmia or patient concern, thereby enhancing diagnostic specificity of cardiac rhythm disorders and providing physiological context to improve diagnostic ability. In a further embodiment, diagnostically relevant cardiac events can be identified and the R-R interval plot can be constructed with a cardiac event centered in the middle (or other location) of the plot, which thereby allows pre- and post-event heart rhythm data to be contextually "framed" through the pinpoint and intermediate ECG data views. Other durations, intervals and presentations of ECG data are possible, including allowing the physician or viewer to select or scroll through the raw ECG data to advance the ECG data together with the R-R interval data, allowing context to be selected by the viewer.

Figure 5:
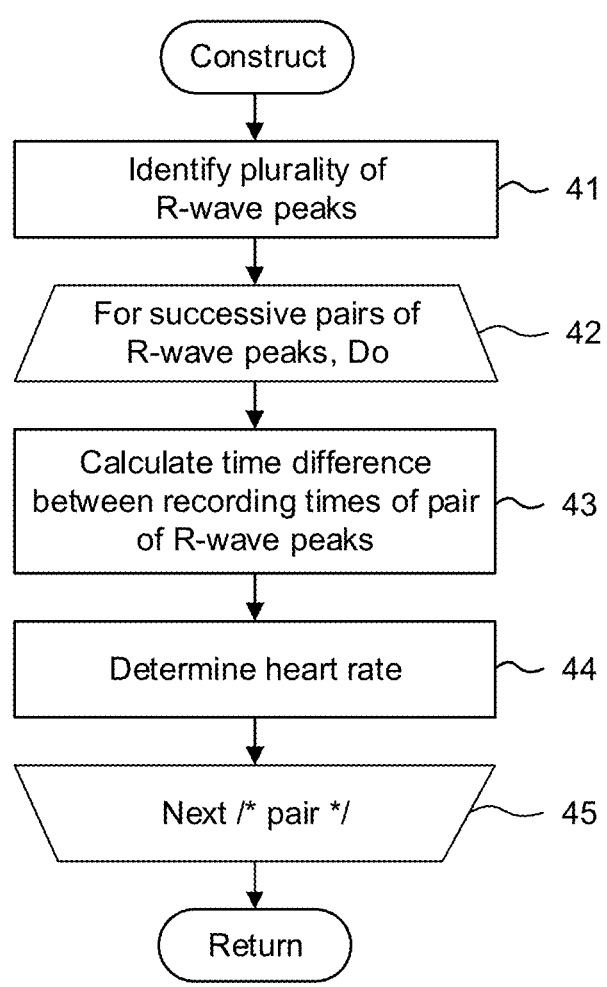
FIG. 5 is a flow diagram showing a routine for constructing an extended-duration R-R interval plot for use in the routine of FIG. 4.

The extended-duration R-R interval plot presents beat-to-beat heart rate variability in a format that is intuitive and contextual, yet condensed. The format of the R-R interval plot is selected to optimize visualization of cardiac events in a compressed, yet understandable field of view, that allows for compact presentation of the data akin to a cardiologists understanding of clinical events. FIG. 5 is a flow diagram showing a routine 40 for constructing an extended-duration R-R interval plot for use in the routine 30 of FIG. 4. The duration of the R-R interval plot can vary from less than one minute to the entire duration of the recording. Thus, a plurality of R-wave peaks is first selected out of the vector of ECG data (step 41) appropriate to the duration of the R-R interval plot to be constructed. For successive pairs of the R-wave peaks (steps 42-43), the difference between the recording times of the R-peaks is calculated (step 43). Each recording time difference represents the length of one heartbeat. The heart rate associated with the recording time difference is determined by taking an inverse of the recording time difference and normalizing the inverse to beats per minute (step 44). Taking the inverse of the recording time difference yields a heart rate expressed in beats per second, which can be adjusted by a factor of 60 to provide a heart rate expressed in bpm. Calculation of the differences between the recording times and the associated heart rate continues for all of the remaining pairs of the R-wave peaks (step 44).

The pairings of R-R intervals and associated heart rates are formed into a two-dimensional plot. R-R intervals are plotted along the x-axis and associated heart rates are plotted along the y-axis. The range and scale of the y-axis (heart rate) can be adjusted according to the range and frequency of normal or patient-specific heart rates, so as to increase the visual distinctions between the heart rates that correspond to different R-R intervals. In one embodiment, the y-axis of the R-R interval plot has a range of 20 to 300 beats per minute and R-R intervals corresponding to heart rates falling extremely outside of this range are excluded to allow easy visualization of 99+% of the heart rate possibilities. To encompass all heart rates theoretically possible, 0 to 350 bpm, would alter the practical visibility of the interval range for the vast majority of events. (Note that these extreme rates remain visible in the ECG.)

In a further embodiment, they-axis has a non-linear scale that is calculated as a function of the x-axis (R-R interval), such that:

$$y = \left(\frac{x - \min \text{bpm}}{\max \text{bpm} - \min \text{bpm}}\right)^n$$

where x is the time difference, min bpm is the minimum heart rate, max bpm is the maximum heart rate, and n<1. The non-linear scale of the y-axis accentuates the spatial distance between successive heart rates when heart rate is low. For example, when n=2, the spatial difference between 50 and 60 bpm is 32% larger than the spatial difference between 90 bpm and 100 bpm, and 68% larger than the spatial difference between 150 bpm and 160 bpm. As a result the overall effect is to accentuate the spatial differences in frequently-occurring ranges of heart rate and de-emphasize the spatial differential in ranges of heart rate where a deviation from norm would have been apparent, thus maximizing the spatial efficiency in data presentation. The goal is to show cardiac events in a simple, small visual contextual format. Larger scales and larger formats bely the practical limits of single-page presentations for the easy visualization at a glance by the busy physician. The visual distinctions between the heart rates that correspond to different R-R intervals stand out, especially when plotted on a non-linear scale. In this configuration, three distinct arrhythmia events can be presented in standard 8.5 by 11 inch page formats. However, other formats are possible. Also, other y-axis ranges and scales are possible as may be selected by distinct clinical needs and specific diagnostic requirements.

Figure 6:
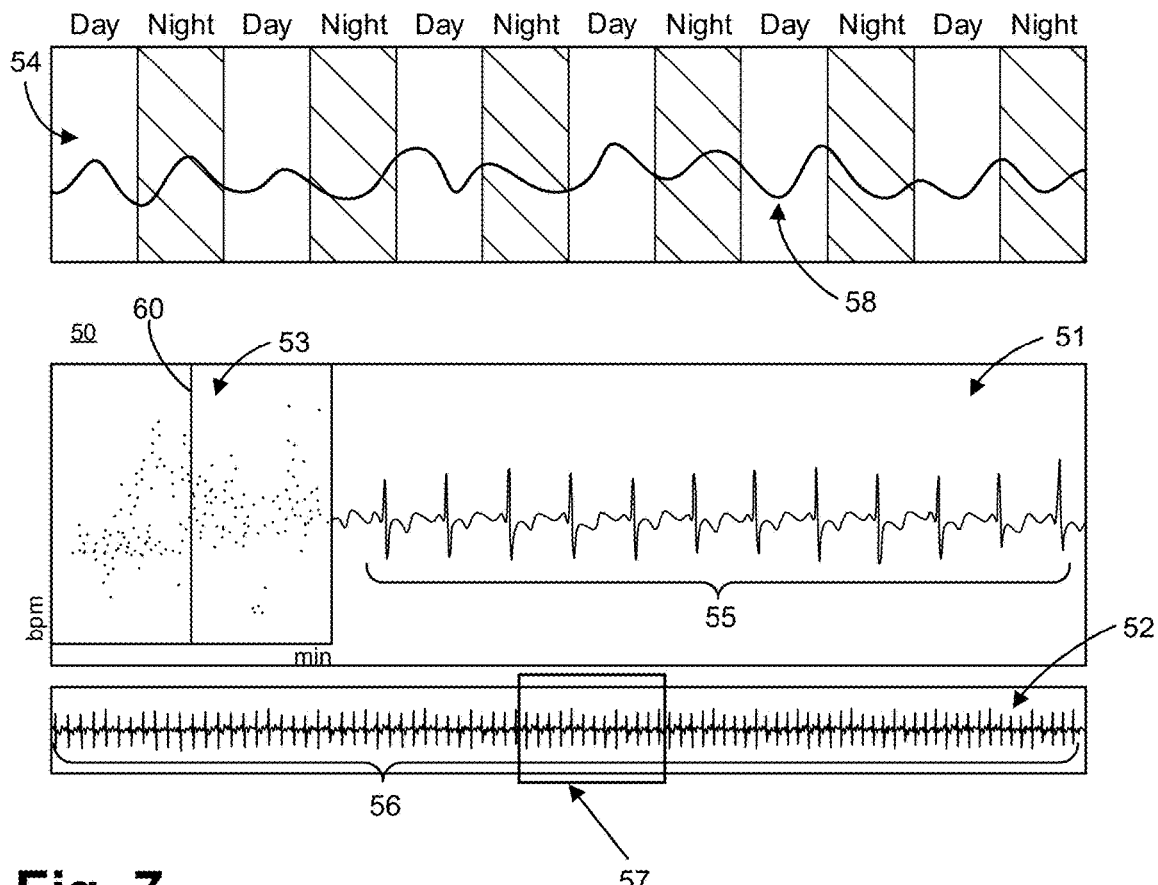
FIG. 6 is a diagram showing, by way of example, a diagnostic composite plot generated by the method of FIG. 3.

The diagnostic composite plot includes a single, long range view of R-R interval data and a pair of pinpoint ECG data views that together help to facilitate rhythm disorder diagnosis by placing focused long-term heart rate information alongside short-term and medium-term ECG information. Such pairing of ECG and R-R interval data is unique in its ability to inform the physician of events prior to, during and after a cardiovascular event. FIG. 6 is a diagram showing, by way of example, a diagnostic composite plot 50 generated by the method 30 of FIG. 3. Note that the diagnostic composite plot can be tailored to include more than one view of R-R interval data and as many views of contextual ECG data as needed. In a further embodiment, a background information plot presenting an extended far field of related information can be included, such as activity amount, activity intensity, posture, syncope impulse detection, respiratory rate, blood pressure, oxygen saturation ($SpO_2$), blood carbon dioxide level ($pCO_2$), glucose, lung wetness, and temperature. Other forms of background information are possible. In a still further embodiment, background information can be layered on top of or keyed to the diagnostic composite plot 50, particularly at key points of time in the R-R interval data plot, so that the context provided by each item of background information can be readily accessed by the reviewing physician.

The diagnostic composite plot 50 includes an ECG plot presenting a near field (short duration) view 51, an ECG plot presenting an intermediate field (medium duration) view 52, and an R-R interval data plot presenting a far field (extended duration) view 53. The three views 51, 52, 53 are juxtaposed alongside one other to allow quick back and forth referencing of the full context of the heart's normal and abnormal physiology. Typically, a temporal point of reference, which could be a diagnostically relevant cardiac event, patient concern or other indicia, would be identified and centered on the x-axis in all three views. The placement of the temporal point of reference in the middle of all three x-axes enables the ECG data to be temporally keyed to the R-R interval data appearing in the center 60 of the R-R interval data view 53, with a near field view 51 of an ECG displayed at normal (paper-based) recording speed and a far field view 52 that presents the ECG data occurring before and after the center 60. As a result, the near field view 51 provides the ECG data corresponding to the R-R interval data at the center 60 (or other location) in a format that is familiar to all physicians, while the intermediate field view 52 enables presentation of the broader ECG data context going beyond the borders of the near field view 51. In a further embodiment, the center 60 can be slidably adjusted backwards and forwards in time, with the near field view 51 and the far field view 52 of the ECG data automatically or manually adjusting accordingly to stay in context with the R-R interval data view 51. In a still further embodiment, multiple temporal points of reference can be identified with each temporal point of reference being optionally accompanied by one or more dedicated sets of ECG data views.

The collection of plots are conveniently arranged close enough to one another to facilitate printing on a single page of standard sized paper (or physical paper substitute, such as a PDF file), although other layouts of the plots are possible. The far field view 53 is plotted with time in the x-axis and heart rate in the y-axis. The R-R intervals are calculated by measuring the time occurring between successive R-wave peaks. In one embodiment, the far field view 53 presents R-R interval data (expressed as heart rate in bpm) that begins about 20 minutes prior to and ends about 20 minutes following the center 60, although other durations are possible.

The near field view 51 and intermediate field view 52 present ECG data relative to the center 60 of the far field view 53. The near field view 51 provides a pinpoint or short duration view of the ECG data. In one embodiment, the near field view 51 presents ECG data 55 that begins about two seconds prior to and ends about two seconds following the center 60, although other durations are possible. The intermediate field view 52 provides additional contextual ECG information allowing the physician to assess the ECG itself and gather a broader view of the rhythm before and after a "blow-up" of the specific arrhythmia of interest. In one embodiment, the intermediate field view 52 presents ECG data 56 that begins about 12 seconds prior to and ends about 12 seconds following the center 60, although other durations are possible. For convenience, the eight-second interval of the ECG data 56 in the intermediate field view 52 that makes up the ECG data 56 in the near field view 51 is visually highlighted, here, with a surrounding box 57. In addition, other views of the ECG data, either in addition to or in lieu of the near field view 51 and the far field view 52 are possible. Optionally, an ECG plot presenting an extended far field view 54 of the background information can be included in the diagnostic composite plot 50. In one embodiment, the background information is presented as average heart rate with day and night periods 58 alternately shaded along the x-axis. Other types of background information, such as activity amount, activity intensity, posture, syncope impulse detection, respiratory rate, blood pressure, oxygen saturation ($SpO_2$), blood carbon dioxide level ($pCO_2$), glucose, lung wetness, and temperature, are possible.

Figure 7:
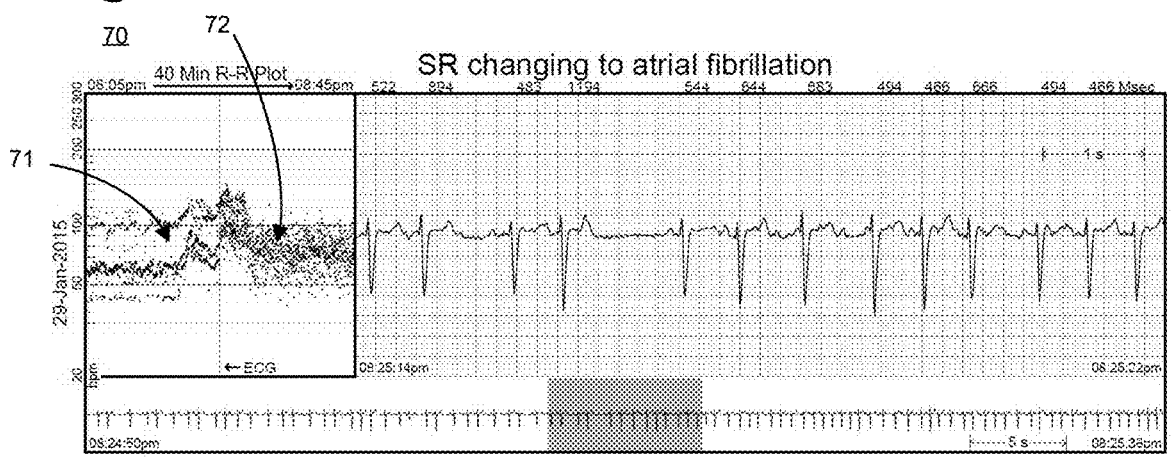
FIG. 7 is a diagram showing, by way of example, a diagnostic composite plot for facilitating the diagnosis of sinus rhythm (SR) transitioning into atrial fibrillation (AF).

Examples of the diagnostic composite plot as applied to specific forms of cardiac rhythm disorders will now be discussed. These examples help to illustrate the distinctive weightings that accompany different forms of rhythm disorders and the R-R interval and ECG waveform deflection context with which they occur. FIG. 7 is a diagram showing, by way of example, a diagnostic composite plot 70 for facilitating the diagnosis of sinus rhythm (SR) transitioning into AF. SR is indicated through the presence of a reasonably steady baseline, but with subsidiary lines of premature beats and their compensatory pauses. SR manifests as a shadowing 71 of a high heart rate line and a low heart rate line. AF is characterized by irregular heartbeats with a somewhat random variation of R-R intervals, although within a limited range and concentrating in a Gaussian-like distribution pattern around a mean that varies over time. Such characteristics can also be distinct from the more random nature of noise. Although AF can be diagnosed by viewing a near field view 51 of ECG data showing heartbeats with reversed P-wave and irregular R-R intervals, this approach may be unclear when viewing "snippets" of ECG data, especially when associated with poor quality ECG signals. The presence of AF can also be confirmed through a far field view 53 of R-R interval data, in which the R-R intervals assume superficially appearing disorganized, spread-out and decentralized scattered cloud 72 along the x-axis, in comparison to a concentrated, darkened line typical of a more organized cardiac rhythm.

Figure 8:
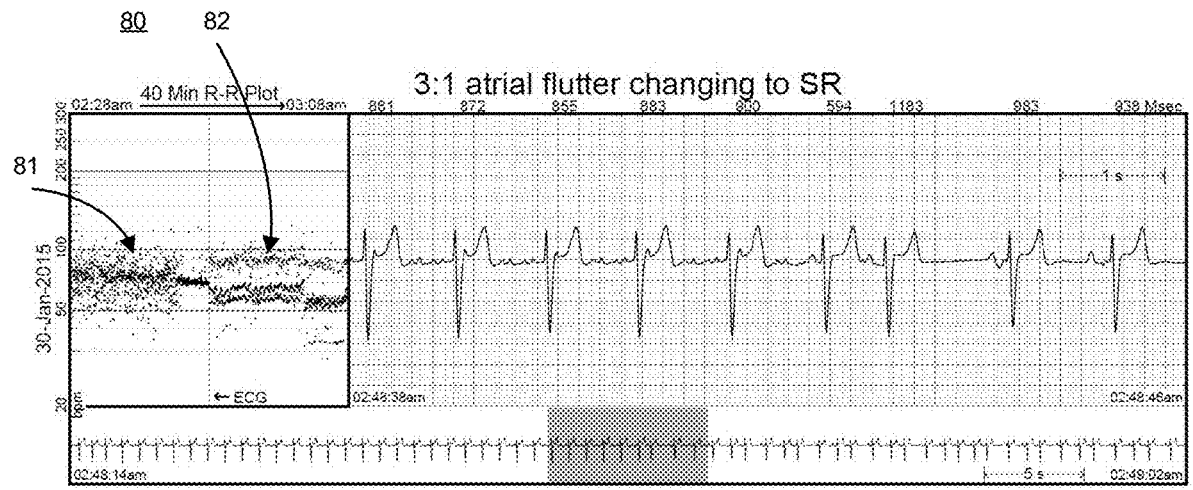
FIG. 8 is a diagram showing, by way of example, a diagnostic composite plot for facilitating the diagnosis of 3:1 atrial flutter (AFL) transitioning into SR.

FIG. 8 is a diagram showing, by way of example, a diagnostic composite plot 80 for facilitating the diagnosis of 3:1 atrial flutter (AFL) transitioning into SR with frequent premature ectopic atrial beats. In the initial part of the R-R interval plot, the R-R intervals have a discernible aggregated line in the middle of the cloud 81 when the rhythm has yet to stabilize into a set pattern, not quite AF and not quite AFL. Immediately thereafter, a dense line representing firm 3:1 atrial flutter stabilizes the rhythm prior to the transition into SR associated with the presence of two seesawing baselines that result from frequent atrial ectopy causing short coupling intervals and then compensatory long coupling intervals. SR is indicated by the middle of the three lines with a low heart rate line consistent with the compensatory pause (long coupling interval) and a high heart rate line with the shortest coupling interval representing the series of atrial premature beats 82, and thus, at a faster heart rate.

Figure 9:
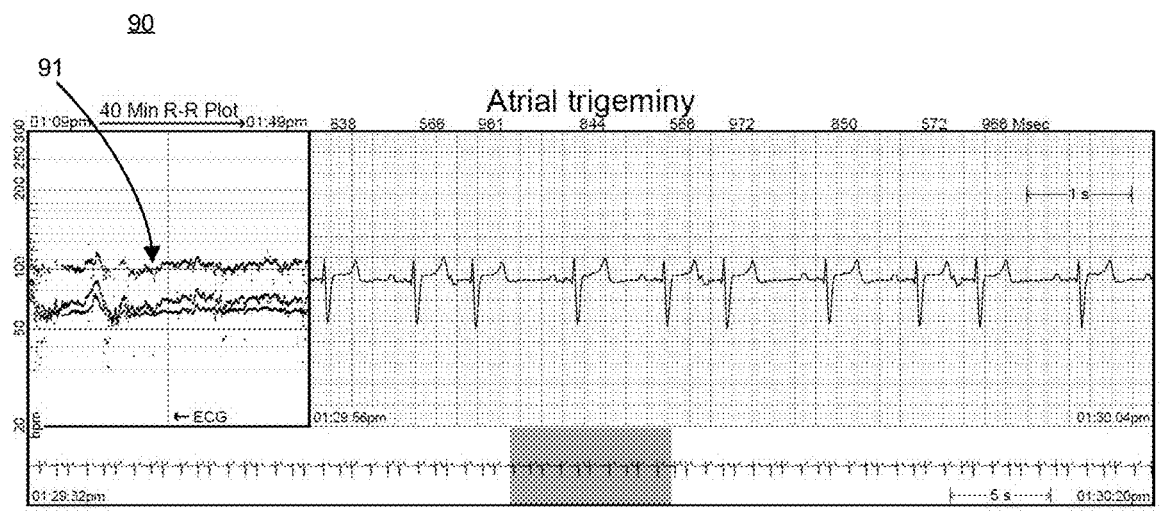
FIG. 9 is a diagram showing, by way of example, a diagnostic composite plot for facilitating the diagnosis of atrial trigeminy.

FIG. 9 is a diagram showing, by way of example, a diagnostic composite plot 90 for facilitating the diagnosis of atrial trigeminy. Atrial trigeminy is characterized by three heartbeat rates appearing intermittently yet reasonably regularly. Although atrial trigeminy can be diagnosed by viewing a near field view 51 of ECG data, the pattern and its clinical impact and frequency is significantly more recognizable in a far field view 53 of R-R interval data, in which a repeating pattern of three distinct heartbeat lines are persistently present and clearly visible 91. This view also provides the physician with a qualitative feel for the frequency of the event troubling the patient that is not discernible from a single ECG strip.

Figure 10:
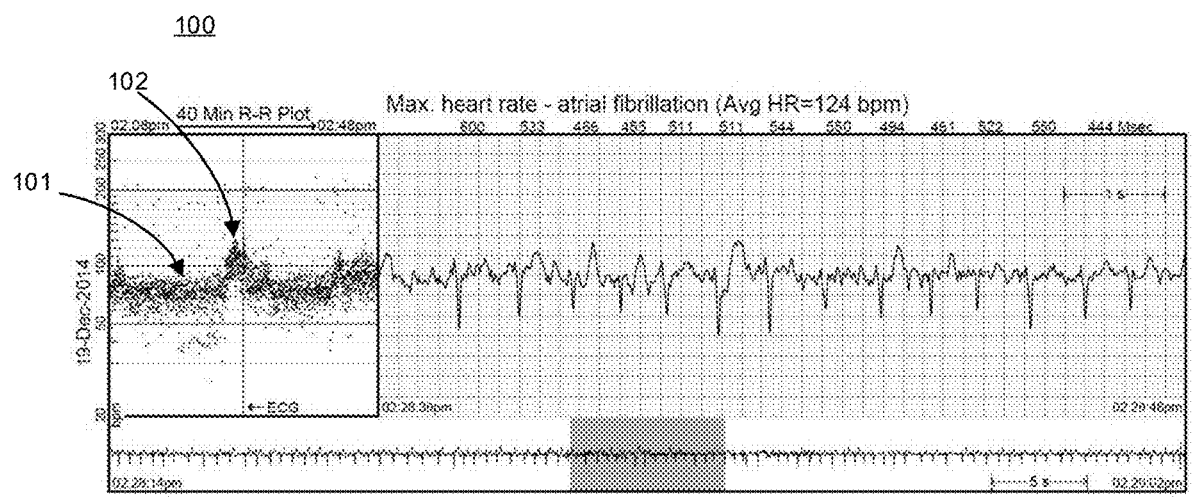
FIG. 10 is a diagram showing, by way of example, a diagnostic composite plot for facilitating the diagnosis of maximum heart rate in an episode of AF during exercise.

FIG. 10 is a diagram showing, by way of example, a diagnostic composite plot 100 for facilitating the diagnosis of maximum heart rate in an episode of AF during exercise.

In a far field view 50 of R-R interval data, AF manifests through a dispersed cloud of dots (Gaussian-like distribution) without a discernible main heart rate line representing regular heartbeats 101. Under exercise, the maximum heartbeat can be located by an increase in heart rate clustered about the cloud 102. In addition, individual dots above the 200 bpm range throughout the entire 40-minute range indicates the maximum heart rate during exercise. The very rapid rise in heart rate can be critical to patient management, as such bumps in rate by exercise can prove dangerous and even trigger cardiac arrest by inducing ventricular fibrillation. Their very presence is easily visualized in the R-R interval data plot, thereby allowing the physician to alter therapy sufficiently to control such potentially damaging rises in heart rate.

Figure 11:
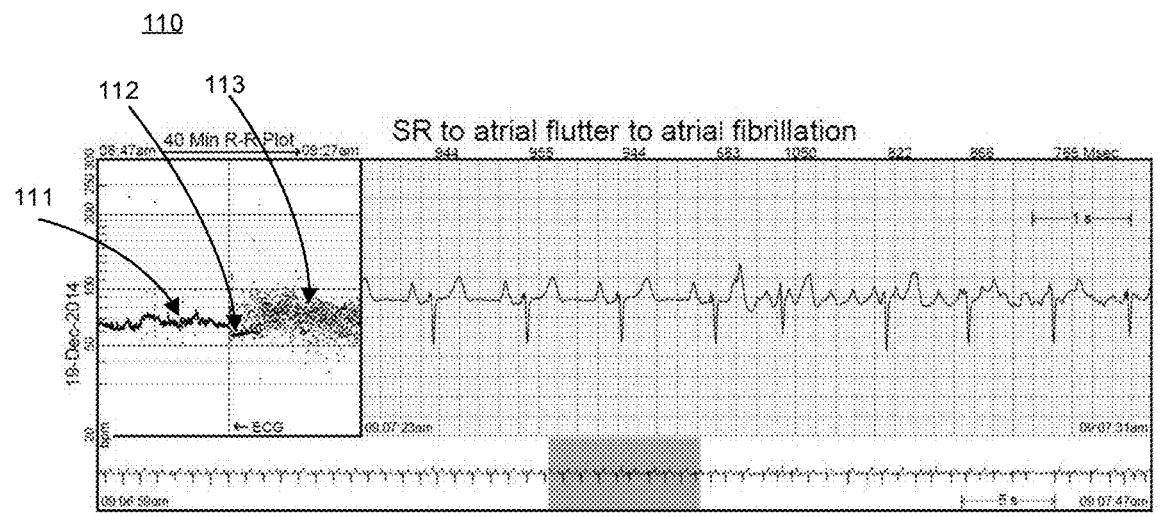
FIG. 11 is a diagram showing, by way of example, a diagnostic composite plot for facilitating the diagnosis of SR transitioning into AFL transitioning into AF.

FIG. 11 is a diagram showing, by way of example, a diagnostic composite plot 110 for facilitating the diagnosis of SR transitioning into AFL transitioning into AF. In a far field view 53 of R-R interval data, SR manifests as an uneven main heart rate line with a fluctuating height 111. At the onset of AFL, the main heart rate line breaks away at a lower heart rate than the SR main heart rate line 112. The episode of AFL further evolves into AF as characterized by a dispersed cloud of irregular heartbeats without concentrated heart rate lines 113. This view provides critical information to the physician managing AF patients in that, at a glance, the view provides data that tells the physician that the patient's AF may be the consequence of AFL. Such knowledge may alter both drug and procedure therapies, like catheter ablation details of intervention. These two disorders are not interchangeable and generally demand different drug and different catheter ablation approaches.

Figure 12:
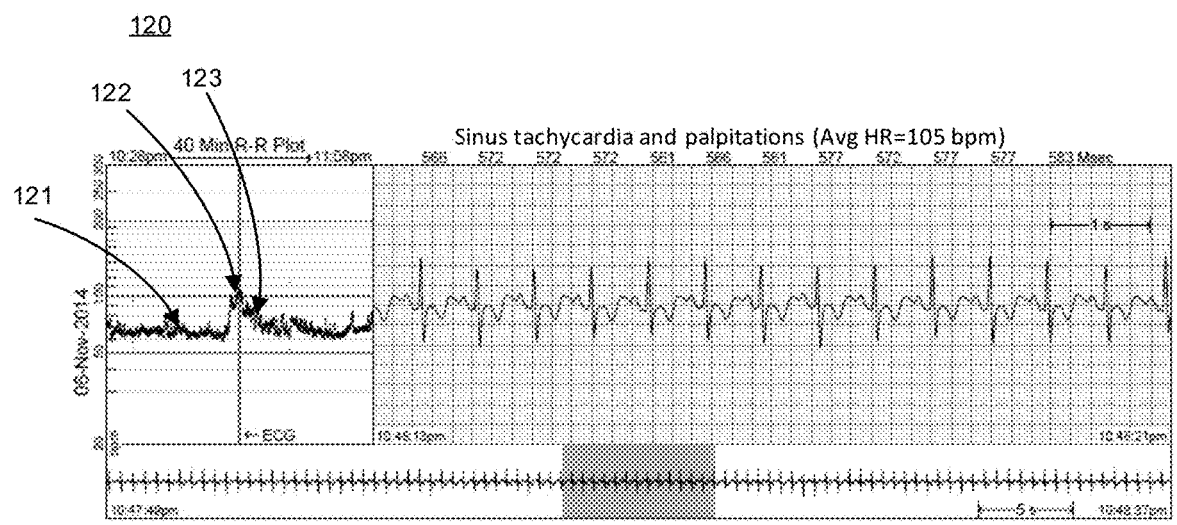
FIG. 12 is a diagram showing, by way of example, a diagnostic composite plot for facilitating the diagnosis of sinus tachycardia and palpitations that occurred during exercise accompanied by a jump in heart rate.

FIG. 12 is a diagram showing, by way of example, a diagnostic composite plot 120 for facilitating the diagnosis of sinus tachycardia and palpitations that occurred during exercise accompanied by a jump in heart rate. In a far field view 50 of R-R interval data, sinus tachycardia is indicated by the presence of a baseline heart rate of about 60 bpm 121 that spikes up to around 100 bpm 122 and gradually slopes down with a wide tail 123, reflecting a sharp rise of heart rates followed by a gradual decline. The associated ECG data in the near field and intermediate field views (not shown) can confirm the rhythm as sinus rhythm and a normal response to exercise. This rhythm, although superficially obvious, was associated with symptoms of palpitations and demonstrates a sensitivity to heart rate fluctuations, rather than a sensitivity to an arrhythmia. This common problem is often dismissed as merely sinus tachycardia, rather than recognizing the context of a changing rate that generated the patient's complaint, a problem, visible only in the R-R interval data plot.

Figure 13:
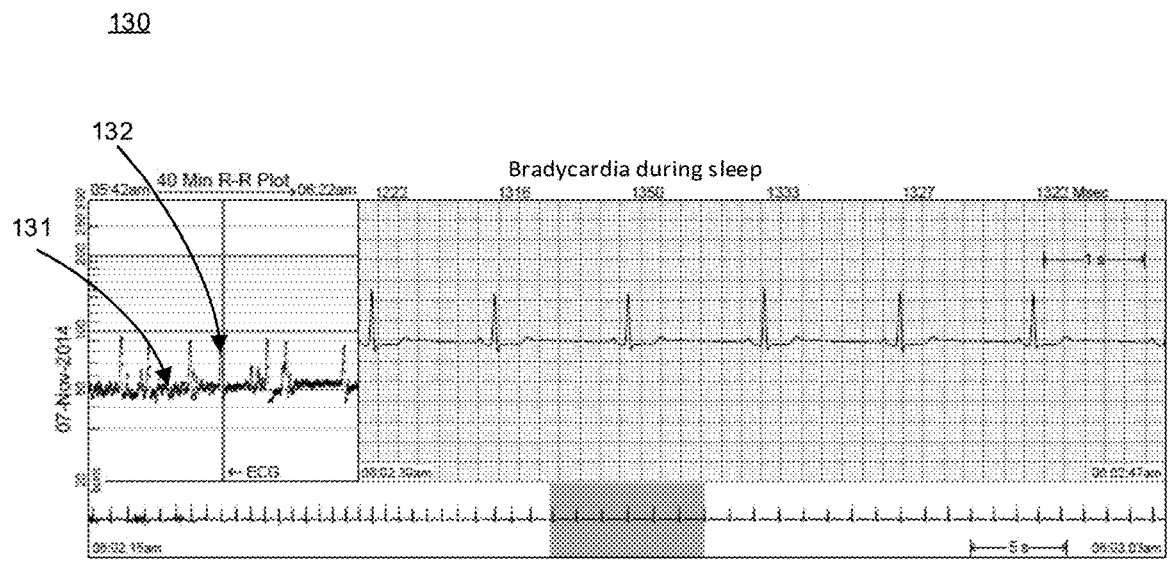
FIG. 13 is a diagram showing, by way of example, a diagnostic composite plot for facilitating the diagnosis of bradycardia.

FIG. 13 is a diagram showing, by way of example, a diagnostic composite plot 90 for facilitating the diagnosis of bradycardia during sleep and a R-R interval pattern characteristic of sleep. Bradycardia refers to a resting heart rate of under 60 bpm. Bradycardia during sleep is often tempered with occasional spikes of rapid heart rate, which can be a secondary compensatory response to dreaming, snoring or sleep apnea. In a far field view 50 of R-R interval data, bradycardia manifests as the presence of a base line heart rate in the range of about 50 bpm 131, coupled with multiple spikes of dots 132 representing intermittent episodes of elevated heart rate. Such elevations in heart rate during a pre-dominantly slower rate may be signs of a cardio-respiratory disorder. Still other applications of the diagnostic composite plot 80 are possible.

The diagnostic composite plots are a tool used by physicians as part of a continuum of cardiac care provisioning that begins with ECG monitoring, continues through diagnostic overread and finally, if medically appropriate, concludes with cardiac rhythm disorder treatment. Each of these steps involve different physical components that collaboratively allow physicians to acquire and visualize R-R interval and ECG data in a way that accurately depicts heart rate variability over time. Further, the data represented by the diagnostic composite plots can be provided to analysis software for cardiac event detection, and patient diagnosis or confirmation. FIG. 14 is a block diagram showing a system 140 for facilitating diagnosis of cardiac rhythm disorders with the aid of a digital computer 150 in accordance with one embodiment. Each diagnostic composite plot 151 is based on ECG data 166 that has either been recorded by a conventional electrocardiograph (not shown) or retrieved or obtained from some other type of ECG monitoring and recording device. Following completion of the ECG monitoring, the ECG data is assembled into a diagnostic composite plot 151, which can be used by a physician to diagnosis and, if required, treat a cardiac rhythm disorder, or for other health care or related purposes.

Each diagnostic composite plot 151 is based on ECG data 166 that has been recorded over a period of observation, which can be for just a short term, such as during a clinic appointment, or over an extended time frame of months. ECG recordation and, in some cases, physiological monitoring can be provided through various types of ECG-capable monitoring ensembles, including a standardized 12-lead ECG setup (not shown), such as used for clinical ECG monitoring, a portable Holter-type ECG recorder for traditional ambulatory ECG monitoring (also not shown), or a wearable ambulatory ECG monitor.

One form of ambulatory ECG monitor 142 particularly suited to monitoring and recording ECG and physiological data employs an electrode patch 143 and a removable reusable (or single use) monitor recorder 144, such as described in commonly-assigned U.S. Pat. No. 9,345,414, issued May 24, 2016, cited supra, and also, further described in detail below with respect to FIGS. 15-18. The electrode patch 143 and monitor recorder 144 are synergistically optimized to capture electrical signals from the propagation of low amplitude, relatively low frequency content cardiac action potentials, particularly the P-waves generated during atrial activation. The ECG monitor 142 sits centrally (in the midline) on the patient's chest along the sternum 169 oriented top-to-bottom. The ECG monitor 142 interfaces to a pair of cutaneous electrodes (not shown) on the electrode patch 143 that are adhered to the patient's skin along the sternal midline (or immediately to either side of the sternum 169). The ECG monitor 142 has a unique narrow "hourglass"-like shape that significantly improves the ability of the monitor to be comfortably worn by the patient 141 for an extended period of time and to cutaneously sense cardiac electric signals, particularly the P-wave (or atrial activity) and, to a lesser extent, the QRS interval signals in the ECG waveforms indicating ventricular activity.

The electrode patch 143 itself is shaped to conform to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends. To counter dislodgment due to tensile and torsional forces, a strain relief can be defined in the electrode patch's flexible circuit using cutouts partially extending transversely from each opposite side of the flexible circuit and continuing longitudinally towards each other to define in 'S'-shaped pattern. In a further embodiment, the electrode patch 143 is made from a type of stretchable spunlace fabric. To counter patient bending motions and prevent disadhesion of the electrode patch 143, the outward-facing aspect of the backing, to which a (non-stretchable) flexible circuit is fixedly attached, stretches at a different rate than the backing's skin-facing aspect, where a skin adhesive removably affixes the electrode patch 143 to the skin. Each of these components are distinctive and allow for comfortable and extended wear, especially by women, where breast mobility would otherwise interfere with ECG monitor use and comfort. Still other forms of ECG monitoring and recording assembles are possible.

When operated standalone, the monitor recorder 142 senses and records the patient's ECG data 166 and physiological data (not shown) into a memory onboard the monitor recorder 144. The recorded data can be downloaded using a download station 147, which could be a dedicated download station 145 that permits the retrieval of stored ECG data 166 and physiological data, if applicable, execution of diagnostics on or programming of the monitor recorder 144, or performance of other functions. To facilitate physical connection with the download station 145, the monitor recorder 144 has a set of electrical contacts (not shown) that enable the monitor recorder 144 to physically interface to a set of terminals 148. In turn, the download station 145 can be operated through user controls 149 to execute a communications or data download program 146 ("Download") or similar program that interacts with the monitor recorder 144 via the physical interface to retrieve the stored ECG data 166. The download station 145 could alternatively be a server, personal computer, tablet or handheld computer, smart mobile device, or purpose-built device designed specific to the task of interfacing with a monitor recorder 144. Still other forms of download station 145 are possible. In a further embodiment, the ECG data 166 from the monitor recorder 144 can be offloaded wirelessly.

The ECG data 166 can be retrieved from the download station 145 using a control program 157 ("Ctl") or analogous application executing on a personal digital computer 156 or other connectable computing device, via a hard wired link 158, wireless link (not shown), or by physical transfer of storage media (not shown). The personal digital computer 156 may also execute middleware (not shown) that converts the ECG data 166 into a format suitable for use by a third-party post-monitoring analysis program. The personal digital computer 156 stores the ECG data 166 along with each patient's electronic medical records (EMRs) 165 in the secure database 64, as further discussed infra. In a further embodiment, the download station 145 is able to directly interface with other devices over a computer communications network 155, which could be a combination of local area and wide area networks, including the Internet or another telecommunications network, over wired or wireless connections.

A client-server model can be employed for ECG data 166 analysis. In this model, a server 62 executes a patient management program 160 ("Mgt") or similar application that accesses the retrieved ECG data 166 and other information in the secure database 164 cataloged with each patient's EMRs 165. The patients' EMRs can be supplemented with other information (not shown), such as medical history, testing results, and so forth, which can be factored into automated diagnosis and treatment. The patient management program 160, or other trusted application, also maintains and safeguards the secure database 164 to limit access to patient EMRs 165 to only authorized parties for appropriate medical or other uses, such as mandated by state or federal law, such as under the Health Insurance Portability and Accountability Act (HIPAA) or per the European Union's Data Protection Directive. Other schemes and safeguards to protect and maintain the integrity of patient EMRs 165 are possible.

In a further embodiment, the wearable monitor 142 can interoperate wirelessly with other wearable or implantable physiology monitors and activity sensors 152, such as activity trackers worn on the wrist or body, and with mobile devices 153, including smart watches and smartphones. Wearable or implantable physiology monitors and activity sensors 152 encompass a wide range of wirelessly interconnectable devices that measure or monitor a patient's physiological data, such as heart rate, temperature, blood pressure, respiratory rate, blood pressure, blood sugar (with or without an appropriate subcutaneous probe), oxygen saturation, minute ventilation, and so on; physical states, such as movement, sleep, footsteps, and the like; and performance, including calories burned or estimated blood glucose level. Frequently, wearable and implantable physiology monitors and activity sensors 152 are capable of wirelessly interfacing with mobile devices 153, particularly smart mobile devices, including so-called "smartphones" and "smart watches," as well as with personal computers and tablet or handheld computers, to download monitoring data either in real-time or in batches through an application ("App") or similar program.

Based on the ECG data 166, physicians can rely on the data as medically certifiable and are able to directly proceed with diagnosing cardiac rhythm disorders and determining the appropriate course of treatment for the patient 141, including undertaking further medical interventions as appropriate. The ECG data 166 can be retrieved by a digital computer 150 over the network 155. A diagnostic composite plot 151 that includes multiple temporal points of reference and a plot of R-R interval data is then constructed based on the ECG data 166, as discussed in detail supra with reference to FIG. 3, and displayed or, alternatively, printed, for use by a physician.

In a further embodiment, the server 159 executes a patient diagnosis program 161 ("Dx") or similar application that can evaluate the ECG data 166 to form a diagnosis of a cardiac rhythm disorder. The patient diagnosis program 161 compares and evaluates the ECG data 166 to a set of medical diagnostic criteria 167, from which a diagnostic overread 162 ("diagnosis") is generated. Each diagnostic overread 162 can include one or more diagnostic findings 168 that can be rated by degree of severity, such as with the automated diagnosis of atrial fibrillation. If at least one of the diagnostic findings 168 for a patient exceed a threshold level of tolerance, which may be tailored to a specific client, disease or medical condition group, or applied to a general patient population, in a still further embodiment, therapeutic treatment ("Therapy") to address diagnosed disorder findings can be generated and, optionally, programmed into a cardiac rhythm therapy delivery device, such as an IMD (not shown), including a pacemaker, implantable cardioverter defibrillator (ICD), or similar devices.

Figure 15:
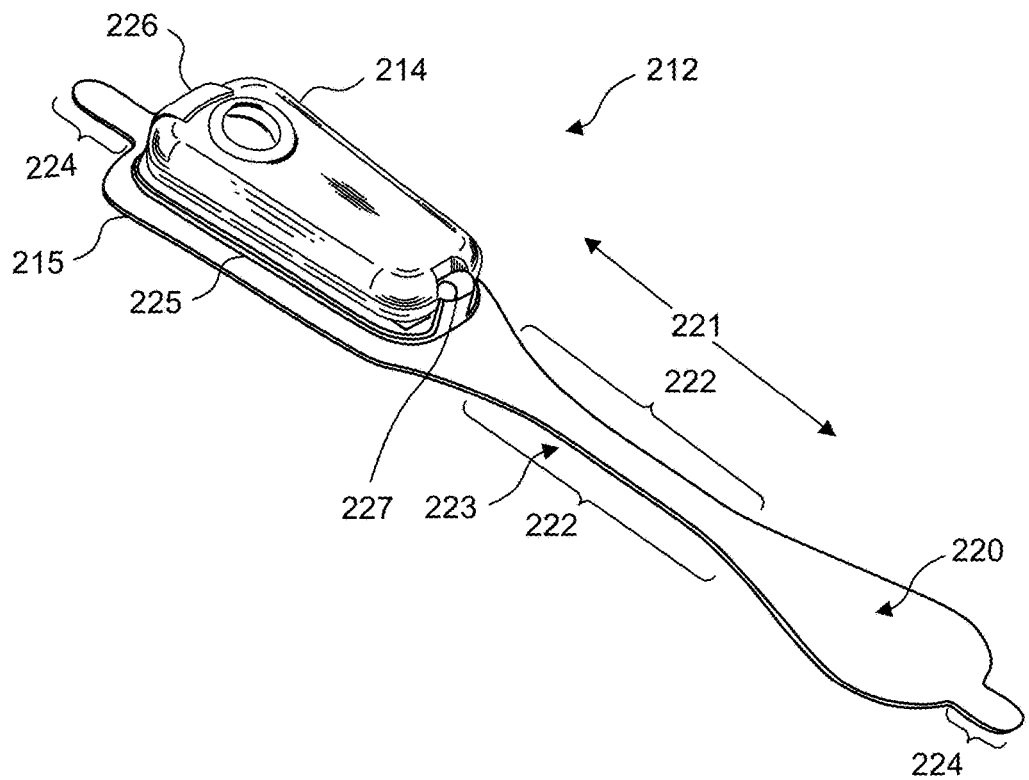
FIG. 15 is a perspective view showing an ECG ambulatory monitor having an extended wear electrode patch with a monitor recorder inserted.

Facilitating diagnosis of cardiac rhythm disorders first requires the collection of ECG data from a patient. In one embodiment, the data can be collected via a wearable ambulatory ECG monitor having an electrode patch and a monitor recorder. The electrode patch is adhered to the patient's skin along the sternal midline or immediately to either side of the sternum to collect the data. A monitor recorder is then snapped into place on the electrode patch using an electro mechanical docking interface to initiate ECG monitoring. FIG. 15 is a perspective view showing an ambulatory ECG monitor 212 having an extended wear electrode patch 215 with a monitor recorder 214 inserted. The body of the electrode patch 215 is preferably constructed using a flexible backing 220 formed as an elongated strip 221 of wrap knit or similar stretchable material about 145 mm long and 32 mm at the widest point with a narrow longitudinal mid-section 223 evenly tapering inward from both sides. However, other lengths and widths are possible. A pair of cut-outs 222 between the distal and proximal ends of the electrode patch 15 create a narrow longitudinal midsection 223 or "isthmus" and defines an elongated "hourglass"-like shape, when viewed from above, such as described in commonly-assigned U.S. Design Pat. No. D744659, issued Dec. 1, 2015, the disclosure of which is incorporated by reference. The upper part of the "hourglass" is sized to allow an electrically non-conductive receptacle 225, that sits on top of the outward-facing surface of the electrode patch 215, to be affixed to the electrode patch 215 with an ECG electrode placed underneath on the patient-facing underside, or contact, surface of the electrode patch 215; the upper part of the "hourglass" has a longer and wider profile (but still rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 215 incorporates features that significantly improve wearability, performance, and patient comfort throughout an extended monitoring period. The entire electrode patch 215 is lightweight in construction, which allows the patch to be resilient to disadhesing or falling off and, critically, to avoid creating distracting discomfort to the patient, even when the patient is asleep. In contrast, the weight of a heavy ECG monitor impedes patient mobility and will cause the monitor to constantly tug downwards and press on the patient's body that can generate skin inflammation with frequent adjustments by the patient needed to maintain comfort.

During every day wear, the electrode patch 215 is subjected to pushing, pulling, and torsional movements, including compressional and torsional forces when the patient bends forward, or tensile and torsional forces when the patient leans backwards. To counter these stress forces, the electrode patch 215 incorporates crimp and strain reliefs, such as described in commonly-assigned U.S. Pat. No. 9,545,204, issued Jan. 17, 2017, the disclosure of which is incorporated by reference. In a still further embodiment, tabs 224 can respectively extend an additional 8 mm to 12 mm beyond the distal and proximal ends of the flexible backing 220 to facilitate with adhering the electrode patch 215 to or removing the electrode patch 215 from the sternum 213. These tabs 224 preferably lack adhesive on the underside, or contact, surface of the electrode patch 215. Still other shapes, cut-outs and conformities to the electrode patch 215 are possible.

The monitor recorder 214 removably and reusably snaps into an electrically non-conductive receptacle 225 during use. The monitor recorder 214 contains electronic circuitry for recording and storing the patient's electrocardiography as sensed via a pair of ECG electrodes provided on the electrode patch 215. The non-conductive receptacle 225 is provided on the top surface of the flexible backing 220 with a retention catch 226 and tension clip 227 molded into the non-conductive receptacle 225 to conformably receive and securely hold the monitor recorder 214 in place.

The electrode patch 215 is generally intended for a single use and is meant to be replaced periodically throughout an extended period of monitoring. However, some types of monitoring may not extend over a period of time long enough to necessitate replacement of the electrode patch 215. In those situations, the monitor recorder 214 and electrode patch 215 can be combined into a single integral assembly.

Figure 16:
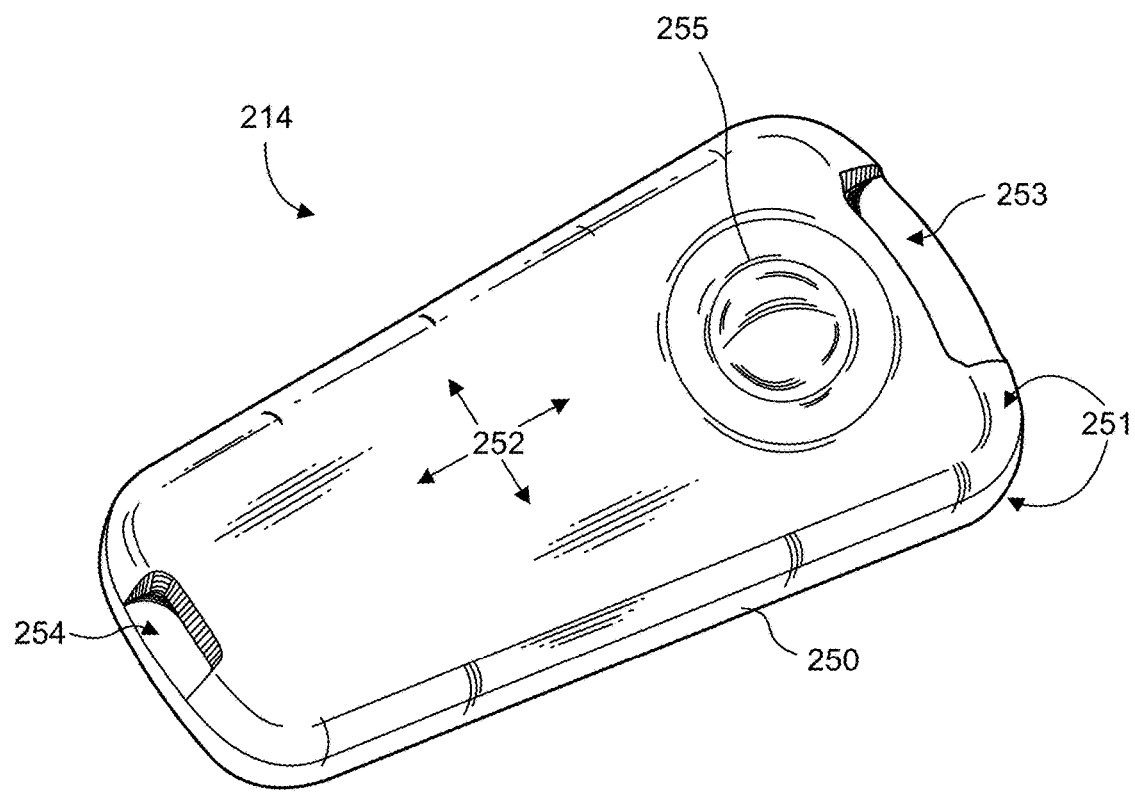
FIG. 16 is a perspective view showing the monitor recorder of FIG. 15.

The monitor recorder 214 includes a sealed housing that snaps into place in the non-conductive receptacle 225. FIG. 16 is a perspective view showing the monitor recorder 214 of FIG. 15. The sealed housing 250 of the monitor recorder 214 can have a rounded isosceles trapezoidal-like shape, when viewed from above, such as described in commonly-assigned U.S. Design Pat. No. D717955, issued Nov. 18, 2014, the disclosure of which is incorporated by reference. The edges 251 along the top and bottom surfaces are rounded for patient comfort. The sealed housing 250 is approximately 47 mm long, 23 mm wide at the widest point, and 7 mm high, excluding a patient-operable tactile-feedback button 255. However, other sizes of the sealed housing are possible.

The sealed housing 250 can be molded out of polycarbonate, ABS, or an alloy of those two materials. The button 255 is waterproof and the button's top outer surface is molded silicon rubber or similar soft pliable material. A retention detent 253 and tension detent 254 are molded along the edges of the top surface of the housing 250 to respectively engage the retention catch 226 and the tension clip 227 molded into non-conductive receptacle 225. Other shapes, features, and conformities of the sealed housing 250 are possible.

The electrode patch 215 is intended to be disposable, while the monitor recorder 214 is designed for reuse and can be transferred to successive electrode patches 215 to ensure continuity of monitoring, if so desired. The monitor recorder 14 can be used only once, but single use effectively wastes the synergistic benefits provided by the combination of the disposable electrode patch and reusable monitor recorder. The placement of the wearable monitor 212 in a location at the sternal midline (or immediately to either side of the sternum) benefits long-term extended wear by removing the requirement that ECG electrodes be continually placed in the same spots on the skin throughout the monitoring period. Instead, the patient is free to place an electrode patch 215 anywhere within the general region of the sternum.

As a result, at any point during ECG monitoring, the patient's skin is able to recover from the wearing of an electrode patch 215, which increases patient comfort and satisfaction, while the monitor recorder 214 ensures ECG monitoring continuity with minimal effort. A monitor recorder 214 is merely unsnapped from a worn out electrode patch 215, the worn out electrode patch 215 is removed from the skin, a new electrode patch 215 is adhered to the skin, possibly in a new spot immediately adjacent to the earlier location, and the same monitor recorder 214 is snapped into the new electrode patch 215 to reinitiate and continue the ECG monitoring.

Figure 17:
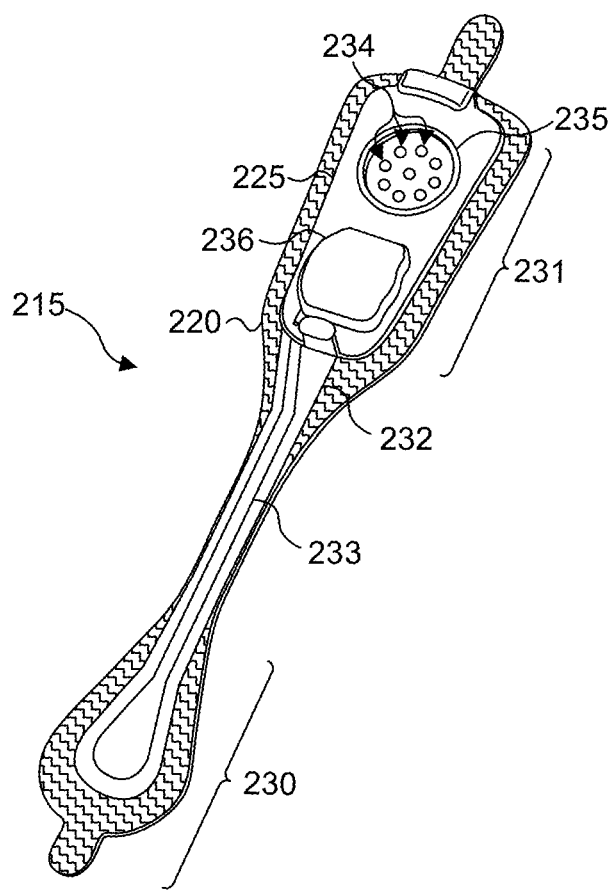
FIG. 17 is a perspective view showing the extended wear electrode patch of FIG. 15 without a monitor recorder inserted.

During use, the electrode patch 215 is first adhered to the skin in the sternal region. FIG. 17 is a perspective view showing the extended wear electrode patch 215 of FIG. 15 without a monitor recorder 214 inserted. A flexible circuit 232 is adhered to each end of the flexible backing 220. A distal circuit trace 233 from the distal end 230 of the flexible backing 220 and a proximal circuit trace (not shown) from the proximal end 231 of the flexible backing 220 electrically couple ECG electrodes (not shown) with a pair of electrical pads 234. In a further embodiment, the distal and proximal circuit traces are replaced with interlaced or sewn-in flexible wires. The electrical pads 234 are provided within a moisture-resistant seal 235 formed on the bottom surface of the non-conductive receptacle 225. When the monitor recorder 214 is securely received into the non-conductive receptacle 225, that is, snapped into place, the electrical pads 234 interface to electrical contacts (not shown) protruding from the bottom surface of the monitor recorder 214. The moisture-resistant seal 235 enables the monitor recorder 214 to be worn at all times, even during showering or other activities that could expose the monitor recorder 214 to moisture or adverse conditions.

In addition, a battery compartment 236 is formed on the bottom surface of the non-conductive receptacle 225. A pair of battery leads (not shown) from the battery compartment 236 to another pair of the electrical pads 234 electrically interface the battery to the monitor recorder 214. The battery contained within the battery compartment 235 is a direct current (DC) power cell and can be replaceable, rechargeable or disposable.

Figure 18:
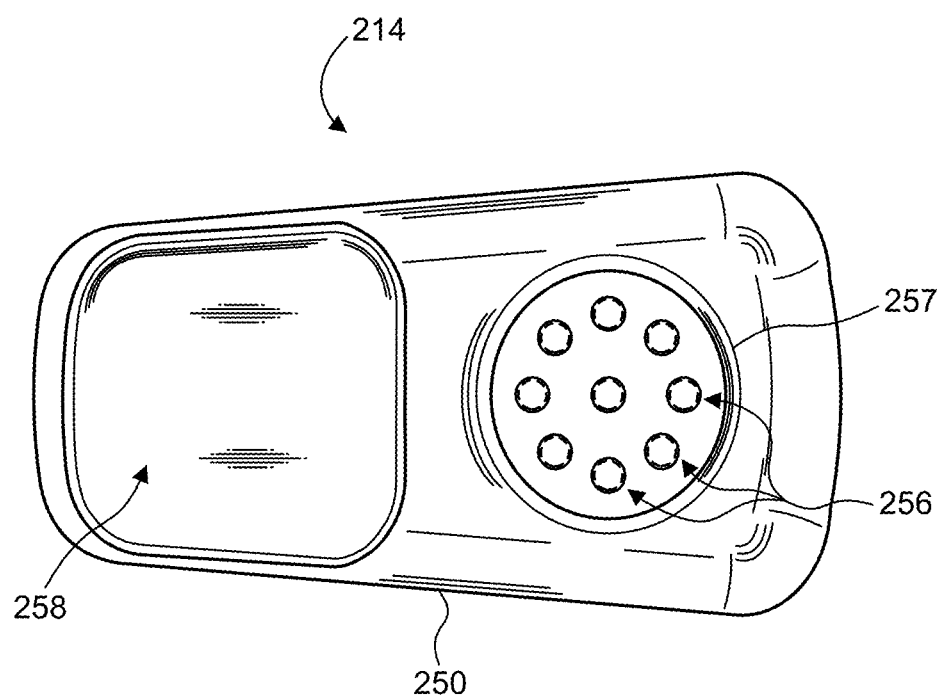
FIG. 18 is a bottom plan view of the monitor recorder of FIG. 15.

The monitor recorder 214 draws power externally from the battery provided in the non-conductive receptacle 225, thereby uniquely obviating the need for the monitor recorder 214 to carry a dedicated power source. FIG. 18 is a bottom plan view of the monitor recorder 214 of FIG. 15. A cavity 258 is formed on the bottom surface of the sealed housing 250 to accommodate the upward projection of the battery compartment 236 from the bottom surface of the non-conductive receptacle 225, when the monitor recorder 214 is secured in place on the non-conductive receptacle 225. A set of electrical contacts 256 protrude from the bottom surface of the sealed housing 250 and are arranged in alignment with the electrical pads 234 provided on the bottom surface of the non-conductive receptacle 225 to establish electrical connections between the electrode patch 215 and the monitor recorder 214. In addition, a seal coupling 257 circumferentially surrounds the set of electrical contacts 256 and securely mates with the moisture-resistant seal 235 formed on the bottom surface of the non-conductive receptacle 225. The battery contained within the battery compartment 236 can be replaceable, rechargeable or disposable. In a further embodiment, the ECG sensing circuitry of the monitor recorder 214 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 214 or onto the non-conductive receptacle 225.

ECG data collected via the ambulatory ECG monitor, such as described above, or another monitor can be provided to a post-monitoring analysis program for cardiac event detection and patient diagnosis. However, prior to analysis by a program, noise can optionally be removed to refine the ECG data for more accurate detection and diagnosis results. For example, ECG data is often interspersed with events that occur while recording and represent device-related events, such as low battery warnings or reset events, which are not interesting to the analysis of the data. Detection and removal of noise not only increases data quality, but reduces an amount of data necessary for analysis, which can result in more accurate and quicker results. Additionally, areas of recorded data near a period of time when the patient presses the feedback button tends to look like noise, but is extremely important for consideration and analysis since the patient believes a cardiac event may be occurring.

Figure 19:
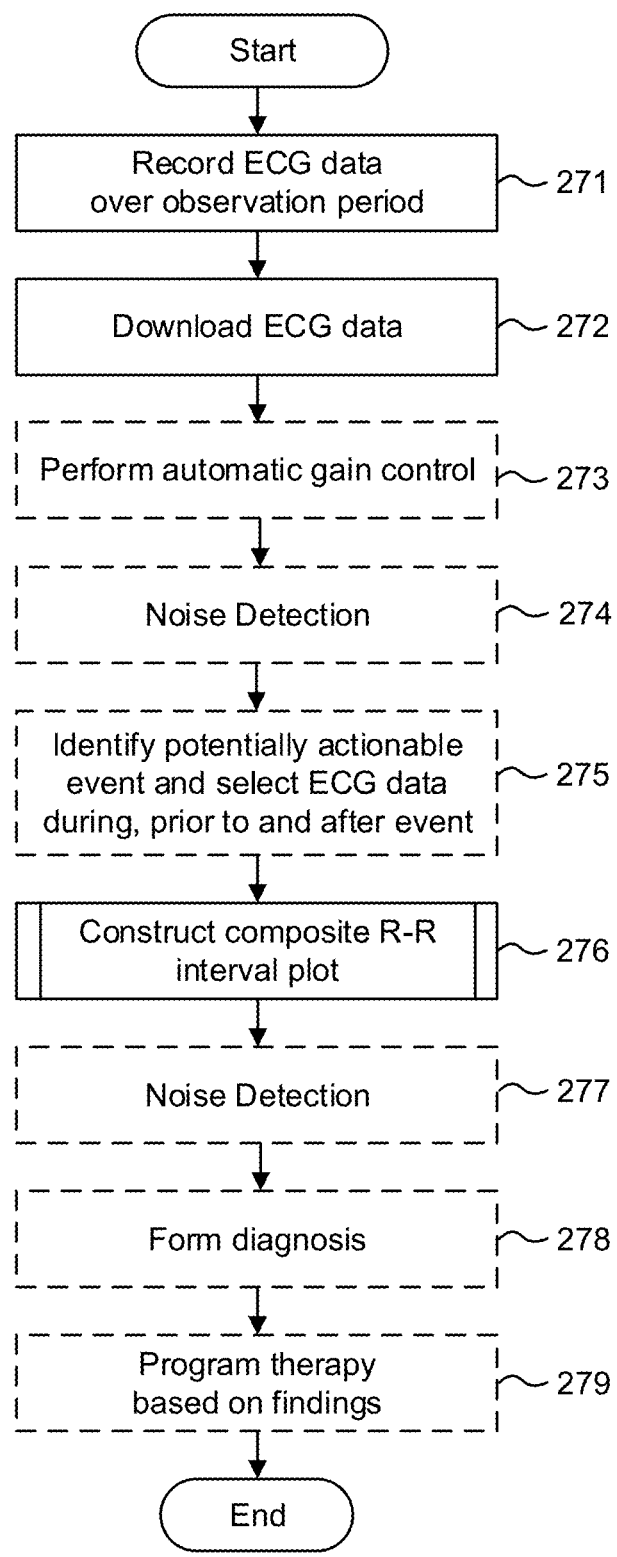
FIG. 19 is a flow diagram showing a method for ECG data classification for use in facilitating diagnosis of cardiac rhythm disorders with the aid of a digital computer.

Noise detection and removal can be performed prior to any processing of the ECG data or after some processing has occurred. FIG. 19 is a flow diagram showing a method 270 for ECG data classification for facilitating diagnosis of cardiac rhythm disorders with the aid of a digital computer. Cutaneous action potentials of a patient are monitored and recorded (block 271) as ECG data over a set time period. Upon completion of the monitoring period, the ECG and any physiological data are downloaded or retrieved into a digital computer (block 272).

Some recorded signals within the collected ECG data are low amplitude and can be incorrectly detected as noise. Optionally, automatic gain control can be applied (block 273) to the recorded signals to place as many as the ECG signals as possible within a normal range, such as from 0.5 to 1.8 mV peak-to-peak, such as described in commonly-assigned U.S. Pat. No. 9,345,414, issued May 24, 2016, the disclosure of which is incorporated by reference. Automatic gain control is generally provided through an AGC module that is implemented as part of a suite of post-processing modules, although automatic gain control could also be provided through standalone software or as part of other forms of ECG visualization and interpretation software. The automatic gain control can be run prior to or after noise detection. If prior, gain control is used to regularize the signal amplitude for noise detection; however, if run after, gain control is used to control the signal amplitude seen by the noise detection analysis software. Alternatively, the signal amplitude is controlled manually by a reading technician.

The gain can be determined by defining a temporal window for automatic gain control. The temporal window has to be long enough to capture at least one heart beat; a five-second temporal window is used, although other durations are possible. The peak-to-peak voltage of each ECG data segment is computed and a single gain factor is applied to the entire signal such that the average signal falls in the center of the preferred range. Alternatively, other statistical values could be used to represent the correlation of the peak-to-peak voltages in the preferred range, either in lieu of or in addition to the average voltage, such as maximum or minimum observed voltage, mean voltage, and so on. Each ECG value in a segment is then processed in an iterative loop. The ECG values are dynamically gained. In one embodiment, the preferred range falls from about 2 mV to 10 mV, although other values could be chosen.

Subsequently, noise detection can optionally be performed (block 274) to refine the ECG data for analysis and use in patient diagnosis. The noise detection can include classifying segments of the ECG data as noise or valid data, as further described below with reference to FIGS. 19-25. A potentially-actionable cardiac event within a vector of the ECG data can be optionally identified and the ECG data during, prior to and after the event can be selected (block 275), as described supra with respect to FIG. 3. In one example, the vector of ECG data can represent a 40-minute (or other duration) time span that is used in constructing the plot of R-R interval data, although other pre-event and post-event time spans are possible. The event could be identified with the assistance of a software package, such as Holter LX Analysis Software, licensed by NorthEast Monitoring, Inc., Maynard, Mass.; IntelliSpace Cardiovascular Image and Information management system, licensed Koninklijke Philips N.V., Amsterdam, Netherlands; MoMe System, licensed by InfoBionic, Lowell, Mass.; Pyramis ECG Management, licensed by Mortara Instrument Inc., Milwaukee, Wis.; ICS Clinical Suite, licensed by Spacelabs Healthcare Inc., Snoqualmie, Wash.; or a customized software package. Alternatively, the potentially-actionable cardiac event could be identified by a physician or technician during review of the ECG data.

Based on the vector of ECG data, a plot of R-R interval data is constructed (block 276) and can be displayed with both near field and far field contextual views of the ECG data, as a diagnostic composite plot, as described supra with respect to FIG. 6. Both views are temporally keyed to an extended duration R-R interval data view that, in one embodiment, is scaled non-linearly to maximize the visual differentiation for frequently-occurring heart rate ranges, such that a single glance allows the physician to make a diagnosis. All three views are presented simultaneously, thereby allowing an interpreting physician to diagnose rhythm and the pre- and post-contextual events leading up to a cardiac rhythm of interest.

Figure 20:
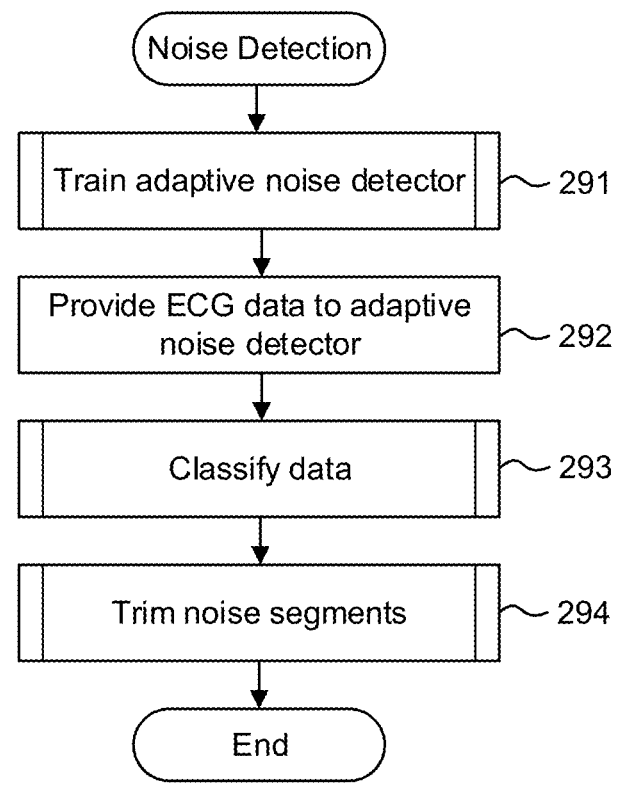
FIG. 20 is a flow diagram showing a method for noise detection.

If not previously performed, noise detection can optionally be performed (block 277) on the R-R interval data to remove data segments classified as noise, as further described below with respect to FIG. 20, to refine the data for further analysis. After, a diagnosis of a cardiac rhythm disorder can optionally be formed (block 278) based on findings made through interpretation of heart rate variability patterns in the diagnostic composite plot. For instance, the heart rate variability patterns in the diagnostic composite plot could be provided to a system that programmatically detects AF by virtue of looking for the classic Gaussian-type distribution on the "cloud" of heart rate variability formed in the plot of R-R interval data, which can be corroborated by the accompanying contextual ECG data. Finally, therapy to address diagnosed disorder findings can optionally be programmed into a cardiac rhythm therapy delivery device (step 279), such as an implantable medical device (IMD) (not shown), including a pacemaker, implantable cardioverter defibrillator (ICD), or similar devices.

A presence of noise in the ECG data can pose problems for cardiologists when diagnosing and caring for patients with possible cardiac arrhythmias. In contrast, identifying and removing noise by classifying segments of the data can greatly increase accuracy of identifying a valid cardiac event. FIG. 20 is a flow diagram showing a method 290 for noise detection. Prior to classification of ECG data, an adaptive noise detector is trained (block 291). In one example, the adaptive noise detector can be implemented by a convolutional neural network that represents a processing device, such as an algorithm executed by a computer processor or actual hardware. Other types of systems are possible.

During training, segments of the ECG data are annotated with a classification of noise or valid data by software analysis or human review. Training is further described in detail below with respect to FIG. 21. Once trained, further ECG data collected from a patient via an ambulatory ECG monitor, such as the monitor described above with respect to FIGS. 15-18, is segmented and provided (block 292) to the trained adaptive noise detector for classification (block 293). However, data from other types of ECG monitors can be used.

Classification of the ECG data segments includes assigning a designation of valid data or noise to each segment. Subsequently, the ECG data segments that correspond with a time frame during which a patient feedback button on the ECG ambulatory monitor is pressed are identified. Those segments classified as noise and that overlap with the timeframe are trimmed (block 294) to remove the data corresponding with the button press. Defining the time frame is further described in detail below with reference to FIG. 23. Finally, all segments classified as noise can be removed from the ECG data prior to further processing. In a further embodiment, the noise data segments can remain with the ECG data; however, during review by analysis software, those segments classified as noise can be ignored.

Figure 21:
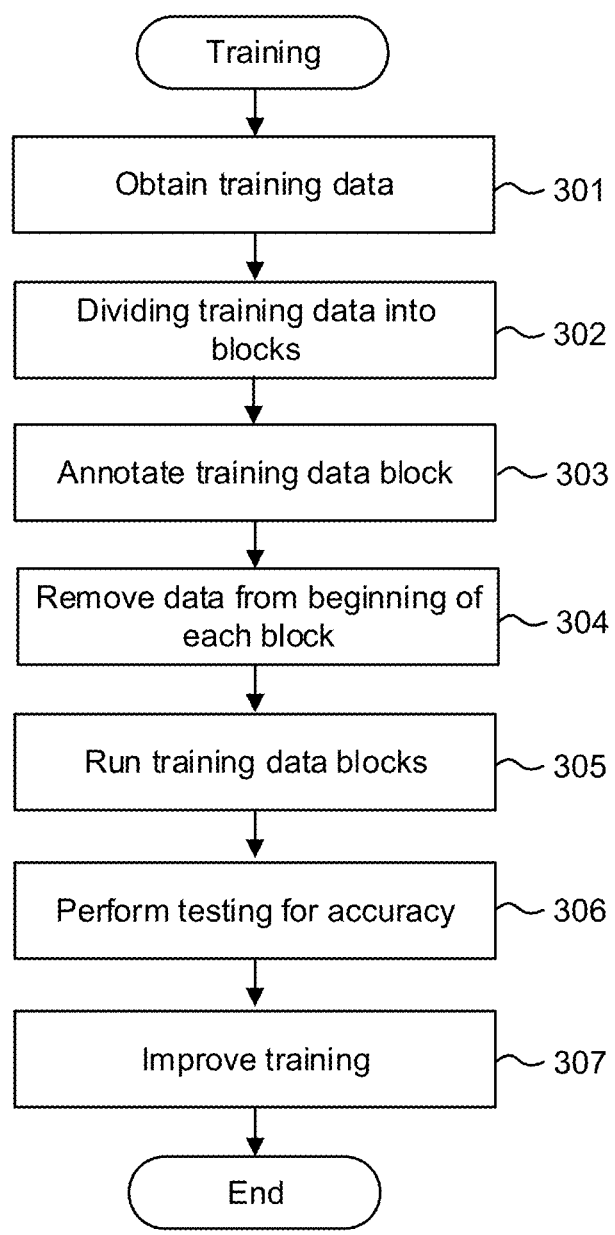
FIG. 21 is a flow diagram showing, by way of example, a method for training an adaptive noise detector.

Accurate classification of the ECG data segments is dependent on training accuracy. FIG. 21 is a flow diagram showing, by way of example, a method 300 for training an adaptive noise detector. ECG training data is obtained (block 301) as data files from ambulatory ECG monitors associated with a group of patients. The patients can be selected randomly or identified based on patient condition. In one embodiment, between 200 and 250 files can be collected from different ECG ambulatory monitors and used as training data. The ambulatory monitors used to collect the ECG data can include the monitor described above with respect to FIGS. 15-18, as well as other types of monitors. The data file collected from each ECG ambulatory monitor can each include up to or more than 64 MB of data.

The training data is divided (block 302) into segments, and regions of the training data are annotated (block 303) with markers for valid data or noise by software analysis, human review, or a combination of software analysis and human review. Specifically, each file from one of the ambulatory ECG monitors is divided into segments. For example, the ECG data from a single file can be divided into over 1500 segments, such that each segment includes between 9-10 seconds of data. However, other numbers of segments and data times represented by each segment are possible, such as segments of data between 2 and 12 seconds. The data can be divided into contiguous segments or alternatively, into overlapping segments. In one embodiment, a neural network views only one segment at a time for detection and thus, each segment should include enough data for a determination of noise. The periodicity of heart activity is an important indicator of non-noise so each segment should include at least a few beats. However, the larger the segment becomes the more good signal will be mis-marked as noise on either side of a real noise identification.

Optionally, a portion of the data at the beginning of each training segment can be removed (block 304) since such data often includes or resembles noise, which could lead to misclassification of the data in that segment. The training data segments are then provided (block 305) to the adaptive noise detector. In one embodiment, the segments of the training data are each provided and run through the adaptive noise detector once. In a further embodiment, the training segments are run multiple times.

After the training data has been run through the adaptive noise detector, testing can be performed (block 306) to determine classification accuracy of the adaptive noise detector. During testing, a set of testing data, such as collected from ECG ambulatory monitors, is run through the trained adaptive noise detector, which classifies the testing data. Additionally, the testing data is annotated manually or via a different program with classifications for noise or valid data. A comparison is made between the annotation of the data and the results of the adaptive noise detector. A number of samples correctly classified is determined and an average accuracy of the testing data is determined. In one embodiment, the average accuracy can be determined and reported after every n number of batches of ECG data. For example, n can represent 100 batches; however, other numbers of batches are possible. The batches can be determined based on an amount of ECG data, a number of ECG ambulatory monitors providing the data, as well as by other metrics. In one embodiment, the batch should be small enough to fit in the memory available, but large enough to amortize startup time. An accuracy threshold can be applied to the average accuracy values and if an average accuracy value or a predetermined number of average accuracy values are below the threshold, further training can be performed (block 307) to increase the accuracy of the adaptive noise detector.

Figure 22:
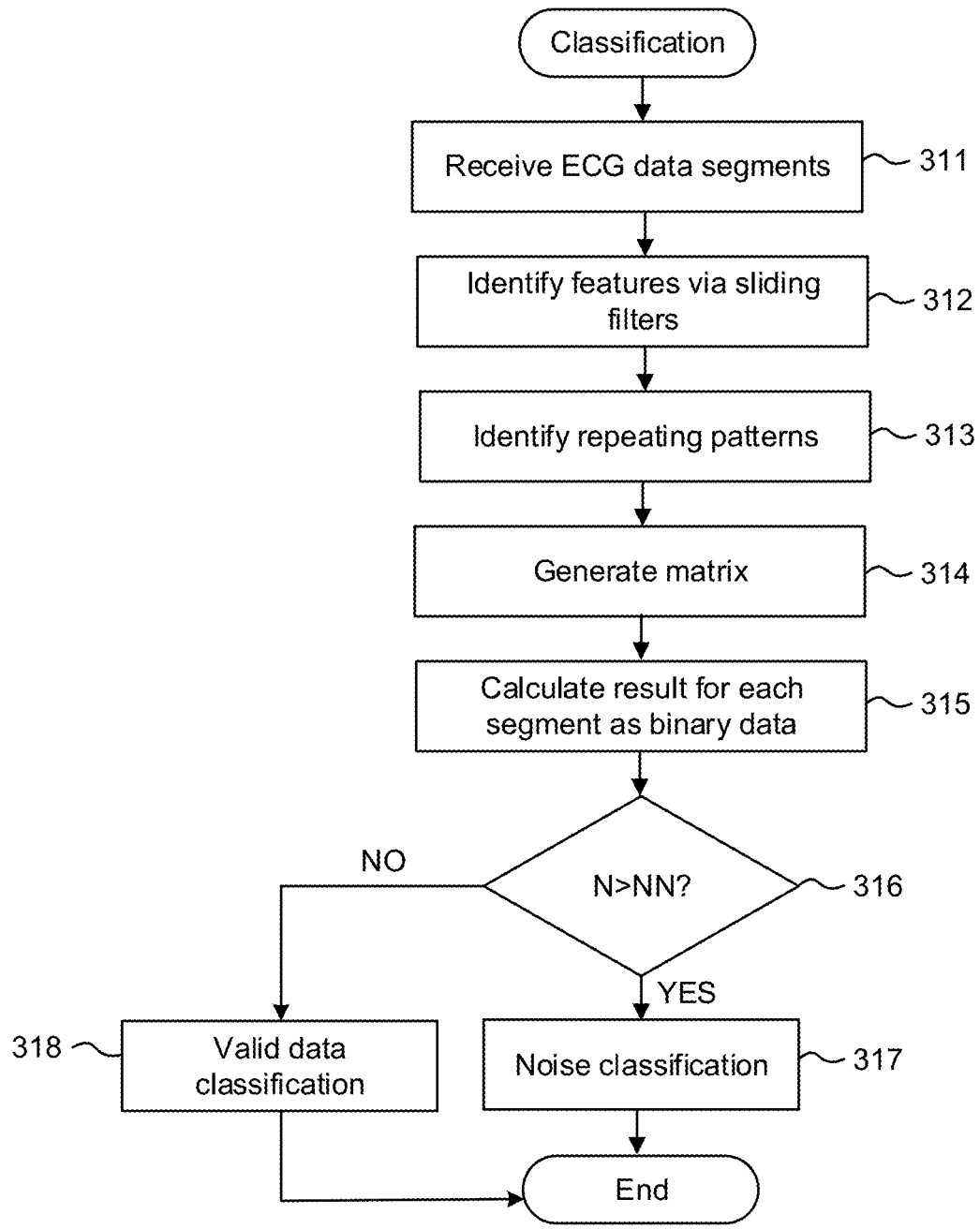
FIG. 22 is a flow diagram showing, by way of example, a method for classification of ECG data.

Once the adaptive noise detector is accurately trained, further ECG data is collected and provided to the detector for classification. FIG. 22 is a flow diagram showing, by way of example, a method 310 for classification of ECG data. The collected ECG data is segmented into blocks, such as described above with respect to the training data of FIG. 21. The ECG data segments are then received (block 311) by the adaptive noise detector, which can be implemented by a convolutional neural network utilizing, for example, a one dimensional formulation for use with ECG data. Additionally, the adaptive noise detector can include hidden layers for performing the classification. In the example described below, two convolutional or pooling hidden layers, and two fully-connected hidden layers are utilized. However, other number of layers are possible.

During the first convolution layer, ECG trace features are identified (block 312) using, for example, sliding filters. Examples of ECG trace features can include two R waves with three P waves located between the R waves and R wave spikes, as well as other types of features that are indicative of a cardiac event, such as an arrhythmia. The features can be automatically learned during the training process and take any form that is learned to be associated with noise or the ECG. In one embodiment, filters for at least 32 features are run against the ECG data. During the second convolution layer, repeating patterns of the features are identified (block 313), including, for example, identifying high numbers of successive R wave spikes.

Next, the data obtained from the second convolution layer is provided to a first fully connected cross-connection layer, which builds (block 314) a matrix with the repeating features representing the columns and matrix multipliers representing rows. An intersection value for each combination of the repeating features and matrix multipliers are listed in the matrix as cross connection weights. Specifically, the intersection value can be determined by multiplying each repeating feature value with a matrix multiplier and scaling the product by a predetermined factor. However, other methods for determining the intersection values are possible.

The second fully connected cross-connection layer utilizes the cross-connection weights from the first fully connected cross-connection layer and multiplies the cross-connection weights by further weights to calculate (block 315) final cross-connection values for each ECG data segment. The final cross-connection values include a noise classification value and a valid data classification value. The noise classification value and the valid data classification value indicate a likelihood that the data segment, respectively, includes noise or does not include noise.

Based on the final cross-connection values, a determination is made as to whether the noise classification value for each data segment exceeds (block 316) the valid data classification value, and if so, the noise classification is assigned (block 317) to that data segment. Otherwise, if the noise classification value does not exceed (block 316) the valid data classification value, a valid data classification is assigned (block 318) to that data segment. As described above, with respect to FIG. 20, the segments classified as noise are removed from the ECG data and the remaining valid data segments are provided for further analysis and patient diagnosis.

However, prior to such analysis, patient identified cardiac events are identified and considered. Patient identified cardiac events are important for use in diagnosis since the patient generally provides feedback when she feels uncomfortable, ill, or is experiencing symptoms resembling a cardiac event. Such feedback is obtained when the patient applies physical pressure to the feedback button located on the monitor recorder of the ECG ambulatory monitor, as shown in FIG. 16.

Often times, though, the physical pressure, from the patient, causes the button press to appear as noise in the recorded data. Due to the importance of the data prior to, during, and after the button press, if the data collected at the time of the button press is marked as noise, some or all of the related data will be removed from further analysis. Thus, to maintain data related to the button press, segments with data that overlap a button press event and that are classified as noise are trimmed to remove the data related to the button from being classified as noise.

Figure 23:
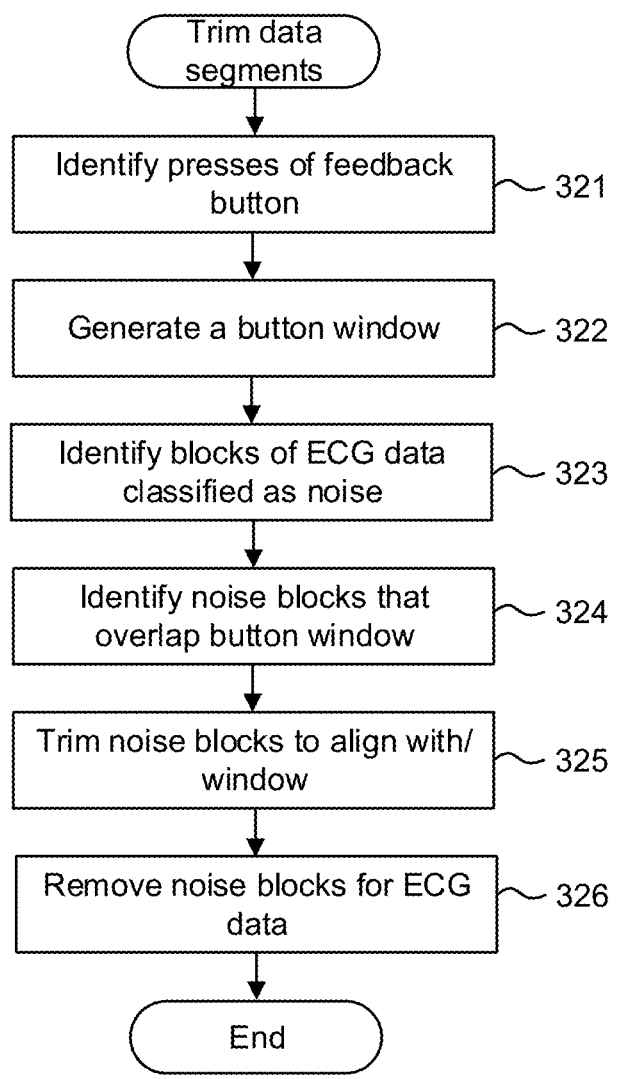
FIG. 23 is a flow diagram showing, by way of example, a method for trimming data segments classified as noise.

The trimming can be performed based on defined button press windows. FIG. 23 is a flow diagram showing, by way of example, a method 320 for trimming data segments classified as noise. Within the ECG data for one or more ECG ambulatory monitors, presses of the patient feedback button are identified (block 321) and marked. For each button press event, a button window is generated (block 322) by identifying a predetermined time before and after each button press event and designating the span of time as a button window. In one example, the predetermined times before and after a button press event can be the same, such as five minutes for a 10 minute window, or a different amount of time. However, in a further embodiment, each of the predetermined time before and after can differ.

The data segments classified as noise are identified (block 323) and compared with the button press windows to further identify (block 324) those noise data segments that overlap a button press window. The overlapping noise data segments are trimmed (block 325) to align with a start or end of the button press window, such that the noise data segment includes no ECG data within the button press window. In one embodiment, the data removed from the noise data segment can be assigned a valid data classification to ensure the data is later reviewed. Further, a noise classification assigned to any data segment that is fully encompassed by the button window is removed so that the data can be considered. Finally, the data segments classified as noise are removed from the ECG data, leaving only the data segments classified as valid and the data associated with the button presses for further analysis and use in patient diagnosis.

Figure 24:
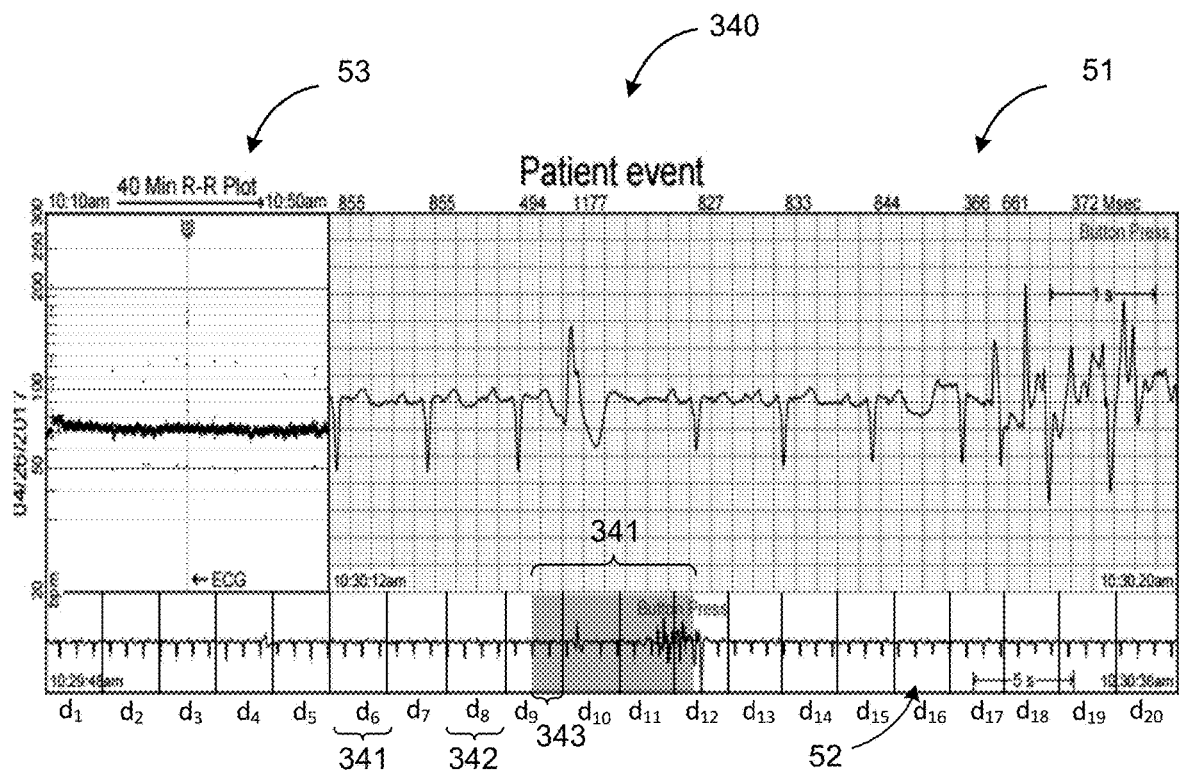
FIG. 24 is a diagram showing, by way of example, a diagnostic composite plot showing data from a button press window.
Figure 25:
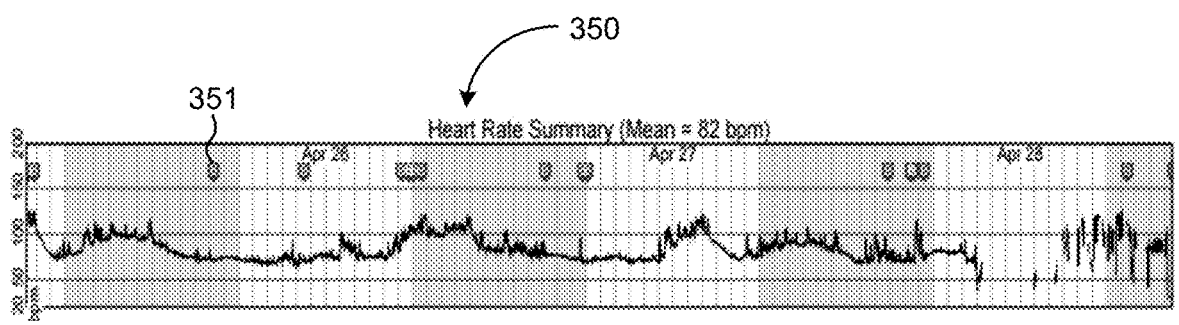
FIG. 25 is a diagram showing, by way of example, a summary graph of data press occurrences.

The button press windows can be displayed in a diagnostic composite plot for analysis by a medical professional. FIG. 24 is a diagram showing, by way of example, a diagnostic composite plot 340 showing data from a button press window. The diagnostic composite plot 340, as described above with respect to FIG. 6, includes an ECG plot presenting a near field (short duration) view 51, an ECG plot presenting an intermediate field (medium duration) view 52, and an R-R interval data plot presenting a far field (extended duration) view 53. A temporal point of reference, such as a button press event, is identified and centered on the x-axis in all three views. The button press event is associated with a button press window 341, which is displayed on the intermediate field view. In a further embodiment, all button presses in the ECG data recording can be displayed. FIG. 25 is a diagram showing, by way of example, a summary graph 350, showing instances of button presses. A summary graph 350 maps all ECG data recorded by the ECG ambulatory monitor over a period up to seven days. The data is displayed and button presses can be identified via an icon 351. Identifying all instances of button presses over a recording period can be useful to identify patterns of symptoms experienced by the patient, which can assist in making a diagnosis.

Returning to the composite plot 340 of FIG. 24, the placement of a single button press window in the middle of the x-axes on all three views enables the ECG data to be temporally keyed to the R-R interval data appearing in the center of the R-R interval data view 53, with a near field view 51 of an ECG displayed at normal (paper-based) recording speed and an intermediate field view 52 that presents the ECG data occurring before and after the center. As a result, the near field view 51 provides the ECG data corresponding to the R-R interval data at the center (or another location), while the intermediate field view 52 enables presentation of the broader ECG data context going beyond the borders of the near field view 51. In a further embodiment, the center can be slidably adjusted backwards and forwards in time, with the near field view 51 and the far field view 52 of the ECG data automatically adjusting accordingly to stay in context with the R-R interval data view 51. In a still further embodiment, multiple temporal points of reference can be identified with each temporal point of reference being optionally accompanied by one or more dedicated sets of ECG data views.

The intermediate field view 52 also displays data segments 342, $d_n$, which each represent a grouping of ECG data that has been classified as valid or noise. In one embodiment, the classification for each data segment 342 can also be displayed. The segments 342 that are assigned a noise classification are compared with the button press window 341. Those noise data segments that overlap with the button press window 341 are trimmed. For example, data segment d8 overlaps with the button press window 341. Accordingly, the overlapping data 343 at the beginning of the button press window is removed from the data segment that is classified as noise, thus trimming the noise data segment. The trimmed data can be added to the next consecutive segment or form a new segment.

Subsequently, in one embodiment, a noise threshold can be applied to the data segments classified as noise to prevent shorts bursts of noise within one such segment from requiring all data in that segment to be removed, since some types of arrhythmias can resemble noise. If the data identified as noise within the noise segment occurs over a period that meets or exceeds the noise threshold, then that noise data segment is removed from the ECG data prior to analysis. However, if the data identified as noise within the noise data segment occurs over a period less than the noise threshold, the noise classification can be removed and the data remains with the ECG data. In one embodiment, each segment is assigned a noise determination of yes or no, with a yes determination indicating noise is present and a no determination indicating no noise is present in the segment. The threshold can be applied to one or more segments and can, in one instance, be equal to the length of a predetermined number of segments. For example, the threshold can be set to 20 seconds based on two 10 second segments of data and can be applied to multiple consecutive segments of data.

Finally, the data segments classified as noise are removed from the ECG data, leaving only the valid data segments and data associated with the button press windows for further analysis. In one embodiment, such data is provided for software analysis or human review for patient diagnosis, including identification of one or more cardiac events.

While the invention has been particularly shown and described as referenced to the embodiments thereof, those skilled in the art will understand that the foregoing and other changes in form and detail may be made therein without departing from the spirit and scope.

What is claimed is:

1. A system for ECG data classification for use in facilitating diagnosis of cardiac rhythm disorders, comprising:
   a patient feedback button on an electrocardiography device associated with a patient;
   a database to store ECG data obtained via the electrocardiography monitor shaped for placement on a patient's chest and a marker identifying patient feedback comprising the ECG data occurring during a press of the feedback button by the patient; and
   a server comprising a central processing unit, memory, an input port to receive the ECG data from the database, and an output port, wherein the central processing unit is configured to:
   divide the ECG data into segments;
   generate a window within at least one of the ECG segments with the marker by identifying a predetermined time before and after one such instance of the patient feedback;
   apply noise detection analysis to the ECG data segments;
   assign one of a noise classification and a valid classification to each segment of ECG data;
   identify at least one ECG data segment assigned the noise classification that includes the window with the ECG data that corresponds with the patient feedback;
   remove the ECG data that corresponds with the window from the identified ECG data segment with the noise classification; and
   retain the removed ECG data that corresponds with the window for analysis.

2. A system in accordance with claim 1, wherein the central processing unit assigns the valid classification to the ECG data that corresponds with the patient feedback.

3. A system in accordance with claim 1, wherein the central processing unit removes a portion of the ECG data located at a beginning of each segment prior to performing the noise detection analysis.

4. A system in accordance with claim 1, wherein the central processing unit calculates a noise data classification value and a valid data classification value for each segment during the noise detection analysis and performs one or more of:
   assigning the noise classification to one of the segments when the noise data classification value exceeds the valid data classification value; and
   assigning the valid classification when the noise data classification value fails to exceed the valid data classification value.

5. A system in accordance with claim 1, wherein the predetermined time before and after the patient feedback comprises one of the same time and different times.

6. A system in accordance with claim 1, wherein the central processing unit removes the noise classification from one such segment of ECG data when the window is the same length as or longer than the segment.

7. A system in accordance with claim 1, wherein the patient feedback comprises a press of a feedback button on the electrocardiography monitor.

8. A system in accordance with claim 1, wherein the ECG data segments are one of overlapping and contiguous.

9. A system in accordance with claim 1, wherein the noise detection analysis is performed via a convolutional neural network.

10. A method for ECG data classification for use in facilitating diagnosis of cardiac rhythm disorders, comprising:
monitoring an electrocardiography monitor with a feedback button for placement on a patient's chest;
storing ECG data obtained via the electrocardiography monitor in a database;
storing in the database the ECG data and a marker identifying patient feedback comprising the ECG data occurring during a press of the feedback button by the patient;
performing by a server, the following:
dividing the ECG data into segments;
generating a window within at least one of the ECG segments with the marker by identifying a predetermined time before and after one such instance of the patient feedback;
applying noise detection analysis to the ECG data segments;
assigning one of a noise classification and a valid classification to each segment of ECG data;
identifying at least one ECG data segment assigned the noise classification that includes the window with the ECG data that corresponds with the patient feedback;
removing the ECG data that corresponds with the window from the identified ECG data segment with the noise classification; and
retaining the removed ECG data that corresponds with the window for analysis.

11. A method in accordance with claim 10, further comprising:
assigning the valid classification to the ECG data that corresponds with the patient feedback.

12. A method in accordance with claim 10, further comprising:
removing a portion of the ECG data located at a beginning of each segment prior to performing the noise detection analysis.

13. A method in accordance with claim 10, further comprising:
calculating a noise data classification value and a valid data classification value for each segment during the noise detection analysis; and
performing one or more of:
assigning the noise classification to one of the segments when the noise data classification value exceeds the valid data classification value; and
assigning the valid classification when the noise data classification value fails to exceed the valid data classification value.

14. A method in accordance with claim 10, wherein the predetermined time before and after the patient feedback comprises one of the same time and different times.

15. A method in accordance with claim 10, further comprising:
removing the noise classification from one such segment of ECG data when the window is the same length as or longer than the segment.

16. A method in accordance with claim 10, wherein the patient feedback comprises a press of a feedback button on the electrocardiography monitor.

17. A method in accordance with claim 10, wherein the ECG data segments are one of overlapping and contiguous.

18. A method in accordance with claim 10, wherein the noise detection analysis is performed via a convolutional neural network.

* * * * *